(12) United States Patent
Endou et al.

(10) Patent No.: US 7,805,983 B2
(45) Date of Patent: Oct. 5, 2010

(54) METHOD FOR MEASURING THE NUMBER OF FINE PARTICLES IN ULTRAPURE WATER AND METHOD FOR MANUFACTURING A FILTRATION DEVICE FOR MEASURING THE NUMBER OF FINE PARTICLES IN ULTRAPURE WATER

(75) Inventors: Mutsuko Endou, Atsugi (JP); Tooru Kusano, Atsugi (JP); Kazunari Akahira, Tokyo (JP); Takashi Ito, Fuji (JP)

(73) Assignees: Nomura Micro Science Co., Ltd., Atsugi-shi (JP); Asahi Kasei Chemicals Corp., Tokyo (JP)

( * ) Notice: Subject to any disclaimer, the term of this patent is extended or adjusted under 35 U.S.C. 154(b) by 282 days.

(21) Appl. No.: 11/883,305

(22) PCT Filed: Jan. 18, 2006

(86) PCT No.: PCT/JP2006/300586

§ 371 (c)(1),
(2), (4) Date: Jul. 30, 2007

(87) PCT Pub. No.: WO2006/080211

PCT Pub. Date: Aug. 3, 2006

(65) Prior Publication Data

US 2008/0168828 A1 Jul. 17, 2008

(30) Foreign Application Priority Data

| Jan. 31, 2005 | (JP) | 2005-023706 |
| Feb. 14, 2005 | (JP) | 2005-036462 |
| Mar. 2, 2005 | (JP) | 2005-058221 |
| Nov. 21, 2005 | (JP) | 2005-336252 |

(51) Int. Cl.
*G01N 30/00* (2006.01)
*B01D 33/21* (2006.01)
(52) U.S. Cl. ............ 73/61.72; 210/500.23; 29/595
(58) Field of Classification Search ............... 73/61.72; 702/128; 210/500.23
See application file for complete search history.

(56) References Cited

U.S. PATENT DOCUMENTS 5,041,220 A * 8/1991 Lee et al. ............... 210/321.8

(Continued)

FOREIGN PATENT DOCUMENTS

EP 0 940 472 A1 9/1999

(Continued)

OTHER PUBLICATIONS

Japanese Industrial Standard, "Testing Methods for Concentration of Fine Particles in Highly Purified Water," JIS K 0554, Japanese Language pp. 1-32.

(Continued)

*Primary Examiner*—Hezron Williams
*Assistant Examiner*—Nathaniel Kolb
(74) *Attorney, Agent, or Firm*—Foley & Lardner LLP

(57) ABSTRACT

A method for measuring the number of fine particles in ultrapure water includes subjecting the ultrapure water to internal pressure filtration through a hollow fiber membrane having a skin layer capable of trapping the fine particles in the ultrapure water at least on an inner surface thereof, exposing the inner surface of the hollow fiber membrane, and measuring the number of fine particles on the exposed inner surface.

3 Claims, 9 Drawing Sheets

U.S. PATENT DOCUMENTS

| | | | |
|---|---|---|---|
| 6,024,872 A * | 2/2000 | Mahendran et al. | 210/500.25 |
| 6,776,172 B2 * | 8/2004 | Okumura | 134/22.11 |
| 7,043,394 B2 * | 5/2006 | Kousaka et al. | 702/128 |
| 7,135,142 B2 * | 11/2006 | Burke et al. | 422/28 |
| 7,186,340 B1 * | 3/2007 | Rittmann et al. | 210/604 |
| 2001/0006783 A1 | 7/2001 | Nogami | |
| 2003/0052055 A1 * | 3/2003 | Akamatsu et al. | 210/500.23 |
| 2003/0057155 A1 * | 3/2003 | Husain et al. | 210/636 |
| 2004/0020845 A1 * | 2/2004 | Suzuki et al. | 210/500.23 |
| 2005/0077227 A1 * | 4/2005 | Kirker et al. | 210/321.69 |

FOREIGN PATENT DOCUMENTS

| | | |
|---|---|---|
| JP | 59-083036 A | 5/1984 |
| JP | 3-008349 Y2 | 2/1991 |
| JP | 3-027254 B2 | 4/1991 |
| JP | 5-032238 Y2 | 8/1993 |
| JP | 8-257380 A | 10/1996 |
| JP | 3040292 B2 | 3/2000 |
| JP | 3040292 B2 * | 5/2000 |
| JP | 3085130 U | 1/2002 |
| JP | 3270722 B2 | 1/2002 |

OTHER PUBLICATIONS

Japanese Industrial Standard, "Testing Methods for Concentration of Fine Particles in Highly Purified Water," JIS K 0554, English language pp. 1-18.

Takashi Ito et al., "Chojunsui Seizo Process ni okeru Maku Bunri Gijutsu," Clean Technology, vol. 8, No. 10, Oct. 1, 1998, pp. 22-25.

"12 Years of UCS—Development of Semiconductor Industry and Furits of 12 Years of UCS," by Semiconductor Basic Technology Research Association, 12-year Committee, Realize Inc., Sep. 30, 2000, pp. 1190-1198.

* cited by examiner

METHOD FOR MEASURING THE NUMBER OF FINE PARTICLES IN ULTRAPURE WATER AND METHOD FOR MANUFACTURING A FILTRATION DEVICE FOR MEASURING THE NUMBER OF FINE PARTICLES IN ULTRAPURE WATER

TECHNICAL FIELD

The present invention relates to a method for measuring the number of fine particles in ultrapure water, a filtration device for measuring the number of fine particles, a method for manufacturing thereof, and a hollow fiber membrane unit for use in the device.

BACKGROUND ART

Conventionally, in order to confirm that the required water quality is maintained in ultrapure water production facilities and the like, the number of fine particles in ultrapure water is measured, for example, by an online method applying laser scattering and sound waves, direct microscopy (for example, see Non-Patent Documents 1, 2) or the like.

As a method for measuring the number of fine particles in ultrapure water using the direct microscopy, a method of causing a sampling pipe to branch off from a pipe through which outlet water of an ultrapure water production system flows, filtering part of the ultrapure water through a filtration membrane for measuring the number of fine particles, trapping the fine particles in the ultrapure water on a membrane surface, subjecting this membrane surface to imaging and image processing by a scanning electron microscope or the like, and counting the number of fine particles is proposed (for example, see Patent Document 1). However, when the number of fine particles is counted, it is practically difficult to directly observe the entire membrane surface by the scanning electron microscope or the like since the filtration membrane has a diameter of about 25 mm. Therefore, usually about 0.001% to about 0.1% of an effective filtration area is actually observed by moving a field of view, and the number of fine particles (number of trapped particles) in the ultrapure water trapped by filtration in the entire effective membrane area is found by calculation.

In recent years, further improvement in water quality is required, and a high requirement is also imposed on the number of fine particles in the ultrapure water being one of water quality control items of the ultrapure water. In some cases, the level of the required water quality is, for example, as high as one or less fine particles with a particle diameter of 0.05 μm or more or 10 or less fine particles with a particle diameter of 0.03 μm or more per 1 ml of ultrapure water.

Along with the above requirement of higher water quality of the ultrapure water, the conventional methods for measuring the number of fine particles have the following problems. For example, when a flat membrane is used as the filtration membrane, blank particles (contamination fine particles) which do not result from the ultrapure water as a measuring object inevitably tend to adhere to the surface of the flat membrane in a membrane manufacturing process, a handling process, and the like, since the membrane surface is exposed. As a result, even in the case of a new flat membrane, for example, $10^5$ particles/cm$^2$ to $10^6$ particles/cm$^2$ of blank particles (contamination fine particles) when the measuring object is a particle with a particle diameter of 0.05 μm or more, or $10^5$ particles/cm$^2$ to $10^7$ particles/cm$^2$ of blank particles (contamination fine particles) when the measuring object is a particle with a particle diameter of 0.03 μm or more adhere to the flat membrane in a stage before it is used.

Therefore, to ensure the analytical precision and lower the analytical lower limit, such a volume of water that the number of trapped particles become the same or more than the number of blank particles (contamination fine particles) needs to be passed. For example, when particles with a particle diameter of 0.05 μm or more are measured at a level of 1 particle/ml, $10^6$ ml=1 m$^3$ of filtration volume is needed. Further, when particles with a particle diameter of 0.03 μm or more are measured at a level of 10 particles/ml, $10^6$ ml=1 m$^3$ of filtration volume is needed. As just described, a large filtration volume is needed, and the filtration time tends to be longer.

Moreover, when particles with such a minute particle diameter are measured using the conventional methods, it is necessary to use a filtration membrane with a smaller pore diameter, but the smaller the pore diameter of the filtration filter through which the ultrapure water is passed, the slower the filtration velocity tends to be. For example, the filtration velocity of the flat membrane filter (MF membrane) with a pore diameter of 0.1 μm is 4.0 ml/min (25° C., 0.75 kgf/cm$^2$), and in contrast, in the case of the MF membrane being the flat membrane with a pore diameter of 0.03 μm, the filtration velocity is 0.1 ml/min (25° C., 0.75 kgf/cm$^2$) and decreases greatly.

Hence, for example, a filtration device which shortens the filtration time by using centrifugal force as a pressurizing means is commercially available. However, in such a device, high rotation centrifugal force of a standard rotational frequency of 12,000 rpm is generated, and thereby the device itself becomes expensive and complicated. Further, since the number of blank particles (number of contamination fine particles) adhering to the membrane surface varies, it is necessary to measure a plurality of the numbers of blank particles (numbers of contamination fine particles) of filtration membranes in the same production lot as the filtration membrane used for sampling and to calculate the mean value and standard deviation of the numbers of blank particles (numbers of contamination fine particles) of the filtration membranes.

Non-Patent Document 1: JISK0554-1990

Non-Patent Document 2: "12 years of UCS—Development of Semiconductor Industry and Fruits of 12 years of UCS" edited by Semiconductor Basic Technology Research Association, 12-year Committee, Realize Inc., Sep. 30, 2000, 1. 190-1. 198 pages Patent Document 1: JP-A 59-83036

DISCLOSURE OF THE INVENTION

Problems to be Solved by the Invention

An object of the present invention is therefore to solve these problems and to provide a method for measuring the number of fine particles in ultrapure water, a filtration device for measuring the number of fine particles, a method for manufacturing thereof, and a hollow fiber membrane unit for use in the device capable of minimization of a measurable particle diameter, improvement in analytical precision, reduction in filtration time, and simplification.

Means for Solving the Problems

As a result of keen investigation to attain the above object, the present inventor et al. have found that by using a hollow fiber membrane having a skin layer capable of trapping more minute fine particles at least on an inner surface thereof when the number of fine particles in ultrapure water is measured, the minimization of a measurable particle diameter, improvement in analytical precision, reduction in filtration time, and simplification are possible and reached the present invention.

Namely, a method for measuring the number of fine particles in ultrapure water of a first aspect of the present invention comprises: subjecting the ultrapure water to internal pressure filtration through a hollow fiber membrane having a skin layer capable of trapping the fine particles in the ultrapure water at least on an inner surface thereof; exposing the inner surface of the hollow fiber membrane; and measuring the number of fine particles on the exposed inner surface.

A method for measuring the number of fine particles in ultrapure water of a second aspect of the present invention is a method for measuring the number of fine particles in ultrapure water using a filtration device for measuring the number of fine particles in ultrapure water comprising: a hollow fiber membrane unit constituted by sealing one end of a hollow fiber membrane having a skin layer capable of trapping the fine particles in the ultrapure water at least on an inner surface thereof and fixing a fixing member to an outer periphery between the sealed portion and an open portion via a resin mold part; a water drain part external cylinder connected to one side of the fixing member while internally equipped with the sealed portion of the hollow fiber membrane; and a water supply part external cylinder connected to the other side of the fixing member while internally equipped with the open portion of the hollow fiber membrane and having a water supply port and a blow water drain port through which the ultrapure water supplied from the water supply port is discharged, the method comprising: passing the ultrapure water from the water supply port of the water supply part external cylinder toward the blow water drain port; subjecting the ultrapure water to internal pressure filtration through the hollow fiber membrane while discharging part of the ultrapure water supplied from the water supply port of the water supply part external cylinder to the blow water drain port; exposing the inner surface of the hollow fiber membrane; and measuring the number of fine particles on the exposed inner surface.

A filtration device for measuring the number of fine particles in ultra pure water of a first aspect of the present invention comprises a hollow fiber membrane unit constituted by sealing one end of a hollow fiber membrane having a skin layer capable of trapping the fine particles in the ultrapure water at least on an inner surface thereof and fixing a fixing member to an outer periphery between the sealed portion and an open portion via a resin mold part.

A method for manufacturing a filtration device for measuring the number of fine particles in ultrapure water of a first aspect of the present invention comprises: forming a hollow fiber membrane unit with both ends sealed by sealing both ends of a hollow fiber membrane having a skin layer capable of trapping the fine particles in the ultrapure water at least on an inner surface thereof and fixing a fixing member to an outer periphery of a central portion thereof with a resin mold; connecting the fixing member of the hollow fiber membrane unit with both ends sealed to a water drain part external cylinder internally equipped with the hollow fiber membrane and reversely passing push water having an antibacterial effect from a water drain port side of the water drain part external cylinder as well as cutting one end of the hollow fiber membrane; and connecting a water supply part external cylinder to the cut one end side of the hollow fiber membrane and reversely passing the push water having the antibacterial effect to fill an interior of the filtration device therewith.

Further, a hollow fiber membrane unit of a first aspect of the present invention is a hollow fiber membrane unit for use in a filtration device for measuring the number of fine particles in ultrapure water and constituted by sealing both ends of a hollow fiber membrane having a skin layer capable of trapping the fine particles in the ultrapure water at least on an inner surface thereof and fixing a fixing member to an outer periphery between the sealed portions at both ends via a resin mold part.

EFFECTS OF THE INVENTION

The above constitutions make it possible to provide a method for measuring the number of fine particles in ultrapure water, a filtration device for measuring the number of fine particles, a method for manufacturing thereof, and a hollow fiber membrane unit for use in the device capable of minimization of a measurable particle diameter, improvement in analytical precision, reduction in filtration time, and simplification when the number of fine particles in the ultrapure water is measured.

BEST MODE FOR CARRYING OUT THE INVENTION

Figure 1:
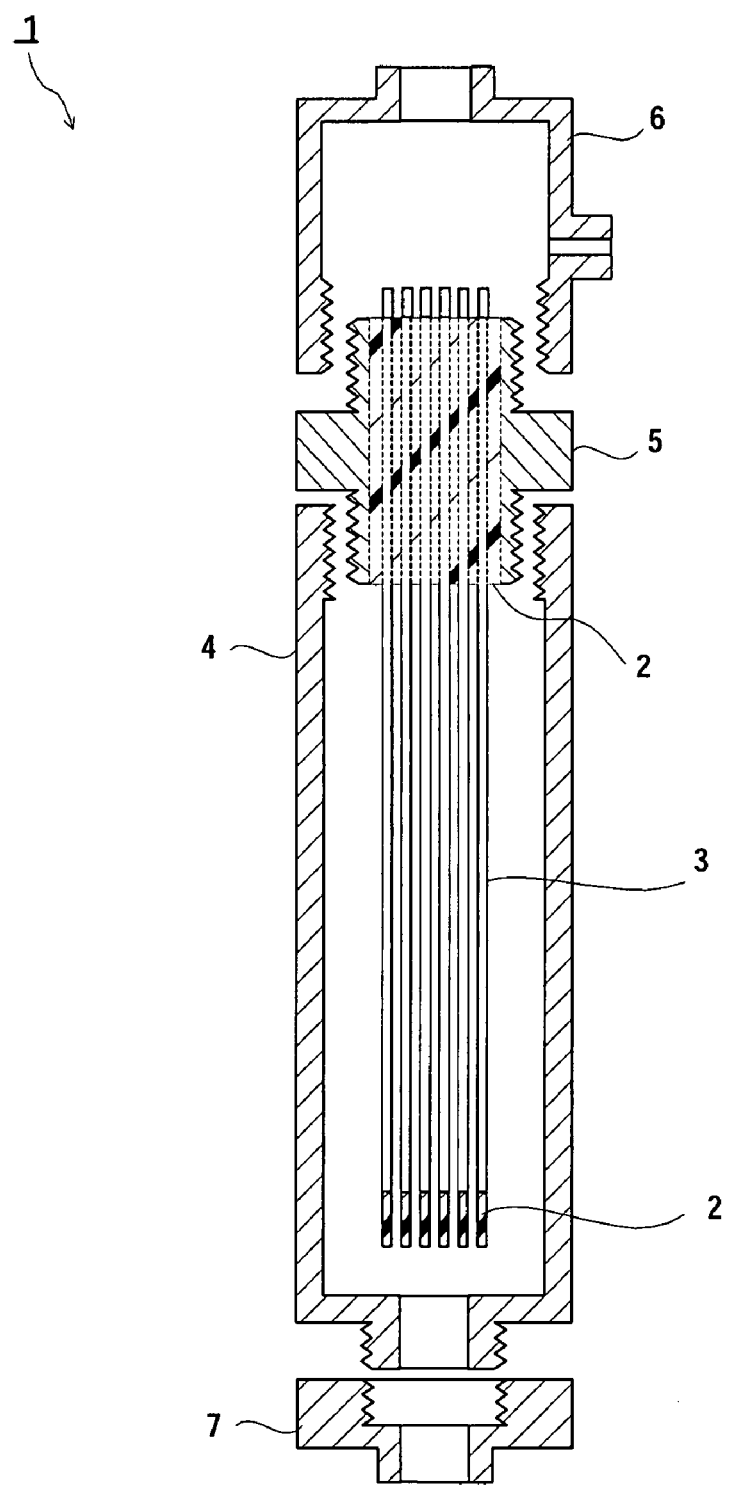
FIG. 1 is a sectional view showing the constitution of a filtration device for measuring the number of fine particles according to a first embodiment.

Next, suitable embodiments of the present invention will be described. It should be understood that the present invention is not limited to the following embodiments.

A hollow fiber membrane of each of the embodiments of the present invention has a skin layer at least on an inner surface thereof. The skin layer has a structure of trapping fine particles with a target particle diameter on its surface when water is passed for filtration in order to count the number of the trapped fine particles in a post-treatment. The hollow fiber membrane is only required to have the skin layer at least on the inner surface, but preferably it has the skin layer on each of the inner and an outer surface since either internal pressure filtration or external pressure filtration is usable, the bursting strength and compressive strength are structurally excellent, a high filtration pressure is settable, and the filtration time can be greatly reduced. Incidentally, in a hollow fiber membrane which does not have the skin layer and traps fine particles by depth filtration instead of screen filtration by which fine particles are trapped on the surface of the skin layer, it is impossible to count the number of the trapped fine particles by observing the membrane surface, so that this hollow fiber membrane cannot be used in the present invention.

The skin layer can trap fine particles with a particle diameter of 10 nm or more and preferably 5 nm or more in ultrapure water. Its pore diameter is only required to be equal to or less than a particle diameter of a fine particle as a measuring object, that is, 10 nm or less, and preferably 5 nm or less. The thinner the skin layer, the higher the transmission rate becomes, so that the thin skin layer is preferable in terms of performance, but a range from 0.1 mm to 0.3 mm is more preferable in terms of strength and durability. Incidentally, as a method for determining the particle diameter of a fine particle which can be trapped, for example, a method shown below is mentioned. First, a sample containing fine particles with a known particle diameter is supplied to a filtration device for measuring the number of fine particles. At this time, two filtration devices are connected in series. A method of observing and comparing trapped particles at a first stage and trapped particles at a second stage (particles which have passed through the first stage) by a scanning electron microscope is mentioned. Alternatively, a method of supplying a sample containing fine particles with a known particle diameter at a known concentration to the filtration device for measuring the number of fine particles and observing and counting the number of trapped particles by the scanning electron microscope may be used.

The hollow fiber membrane diameter is not particularly limited, but since the smaller effective membrane area is better to reduce the necessary filtration volume and shorten the filtration time, the internal diameter is preferably 0.8 mm or less, and particularly from 0.5 mm to 0.8 mm. Further, to improve workability when the number of trapped fine particles is counted, the external diameter is preferably 1.0 mm or more, and particularly from 1.0 mm to 1.9 mm. Its membrane structure may be a symmetric membrane (homogeneous membrane) or an asymmetric membrane (heterogeneous membrane), and may be a lobe-type asymmetric membrane in which a skin layer and a core layer are made of the same material or a composite membrane in which a skin layer and a core layer are made of different materials. The material for the hollow fiber membrane is not particularly limited, and as examples thereof, polyacrylonitrile, polysulfone, polyphenylene sulfone, polyphenylene sulfide sulfone, polyvinylidene fluoride, cellulose acetate, polyethylene, polypropylene, and so on are mentioned, and polyacrylonitrile, polysulfone, polyvinylidene fluoride, cellulose acetate, polyethylene, and, polypropylene are preferable. Among them, materials such as polyacrylonitrile, polysulfone, and polyvinylidene fluoride having high bursting strength and compressive strength and a pressure resistance of 0.5 MPa or more are more preferable since using them, the hollow fiber membrane with a minute pore diameter can be easily manufactured, and the filtration time can be easily shortened. Incidentally, to shorten the filtration time, a filtration capability of 0.8 ml/min/cm$^2$ or more (0.1 MPa, 25° C.) is desirable.

The hollow fiber membrane does not need a support because of its structure, and can be easily handled by being modularized, for example, even when it is washed to remove blank particles (contamination fine particles). Besides, since the hollow fiber membrane is tightly sealed, it need not be washed in a clean room where fine particles in an atmosphere are managed in order to prevent re-contamination after washing. In contrast, the flat membrane is as very thin as several μm to 10 μm to reduce filtration resistance and needs a support when used, and its handling is complicated. Further, in terms of its shape and strength, it is difficult to wash and remove blank particles (contamination fine particles) while preventing fine particle contamination. Furthermore, it is required to be washed in the clean room to prevent re-contamination after washing.

Moreover, in the hollow fiber membrane, the number of blank particles (number of contamination fine particles) adhering to the inner surface thereof is smaller than that in an MF membrane or the like being the conventional flat membrane. Namely, in the case of the flat membrane, both an inner and outer surfaces thereof are exposed, so that fine particles in the atmosphere tends to adhere thereto in a membrane manufacturing process and the like, and hence the membrane surface tends to be contaminated. In contrast, in the case of the hollow fiber membrane, the outer surface side is exposed, while the inner surface side is not exposed, so that the adhesion of fine particles in a membrane manufacturing process and the like can be prevented. For example, when the measuring object is a fine particle with a particle diameter of 0.03 μm or more, $10^5$ particles/cm$^2$ to $10^7$ particles/cm$^2$ of blank particles (contamination fine particles) adhere to the membrane surface of the flat membrane. In contrast, the number of blank particles (number of contamination fine particles) adhering to the outer surface of the hollow fiber membrane having the skin layer on each of the inner and outer surfaces can be reduced to $10^5$ particles/cm$^2$ to $10^6$ particles/cm$^2$, and the number of blank particles (number of contamination fine particles) adhering to the inner surface thereof can be reduced to $10^4$ particles/cm$^2$ to $10^5$ particles/cm$^2$, and more preferably, $10^3$ particles/cm$^2$ to $10^4$ particles/cm$^2$. Consequently, when fine particles are trapped on the inner surface of the hollow fiber membrane, ⅟₁₀₀₀ of filtration volume is sufficient to ensure the same analytical precision as that of the flat membrane, which can greatly shorten the filtration time. Further, if the same filtration volume is filtered, the lower detection limit level can be lowered, and the quantitative analysis of fine particles of 10 particles/L is possible.

Accordingly, as the filtration direction, either external pressure filtration or internal pressure filtration is usable, but in the hollow fiber membrane, the number of blank particles (number of contamination fine particles) on its inner surface is smaller than that on its outer surface as described above, so that it is desirable to use the internal pressure filtration in which fine particles are trapped by the skin layer on the inner surface. The internal pressure filtration makes it possible to reduce the volume of ultrapure water passing through the hollow fiber membrane and thereby shorten the filtration time. Further, as the filtration system, either dead end filtration or cross flow filtration is usable, but the dead end filtration is preferable in order to trap all of fine particles in the supplied ultrapure water.

Incidentally, sample water passed through the filtration membrane is not limited to the ultrapure water as long as it contains fine particles therein and the number of fine particles trapped by the hollow fiber membrane by filtration can be counted.

Next, a filtration device for measuring the number of fine particles in ultrapure water and a method for measuring the number of fine particles using the hollow fiber membrane according to each of the embodiments of the present invention will be described with reference to the drawings.

First Embodiment

Figure 2:
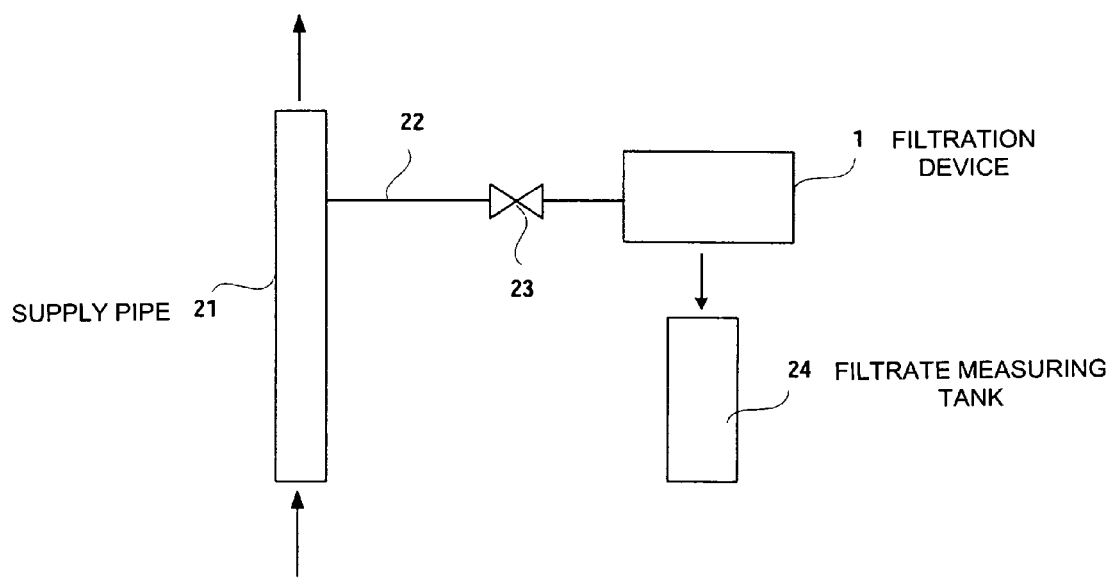
FIG. 2 is a schematic diagram showing an example of a method for measuring the number of fine particles in ultrapure water using the filtration device for measuring the number of fine particles shown in FIG. 1.

A first embodiment of the present invention will be described with reference to FIG. 1 and FIG. 2. FIG. 1 is a sectional view showing the constitution of a filtration device for measuring the number of fine particles according to the first embodiment. FIG. 2 is a schematic diagram showing an example of a method for measuring the number of fine particles in ultrapure water using the filtration device for measuring the number of fine particles shown in FIG. 1.

As shown in FIG. 1, a filtration device for measuring the number of fine particles 1 is fabricated by fixing a hollow fiber membrane 3 with one end sealed with an adhesive 2 such as an epoxy resin to a fixing member such as a nipple 5 with the adhesive 2 (resin mold part), connecting a water supply part external cylinder 6 to one side (open end side of the hollow fiber membrane 3) of the nipple 5, and connecting a water drain part external cylinder 4 (holder) to the other side (sealed side of the hollow fiber membrane 3). A water drain part joint 7 is connected to the water drain part external cylinder 4. This filtration device for measuring the number of fine particles 1 has a (backwashable) structure in which water can be passed in a direction reverse to a filtration direction (internal pressure filtration) to wash and remove blank particles (contamination fine particles) adhering to the membrane surface. Namely, the hollow fiber membrane 3 may be previously backwashed. By backwashing the hollow fiber membrane 3, the blank particles (contamination fine particles) adhering to the inner surface of the hollow fiber membrane can be washed and removed, which makes it possible to further reduce the water-passing capacity and further shorten the filtration time.

Next, an example of the method for measuring the number of fine particles in the ultrapure water using the filtration device for measuring the number of fine particles shown in FIG. 1 will be described using FIG. 2.

The ultrapure water is passed from a supply pipe 21 through which outlet water from ultrapure water production facilities flows to the filtration device for measuring the number of fine particles equipped with the hollow fiber membrane via a sample introducing tube 22 provided with a sampling valve 23. In the filtration device 1, fine particles in the ultrapure water are trapped at room temperature (25° C.) to high temperature (80° or lower) and the ultrapure water is passed until a given water volume is stored in a filtrate measuring tank 24. The filtrate measuring tank 24 is a measuring tank as a measuring means. As the measuring means, any one which can measure a given filtration capacity is available, and as examples thereof, in addition to the measuring tank, a flow integrator and so on are mentioned. Further, a pressuring means by a pump or gas or the like may be provided between the sample introducing tube 22 and the filtration device 1 if necessary. By using the pressurizing means, the filtration velocity can be increased, and the filtration time can be shortened. Furthermore, it is also possible to provide a heating means such as a heater in the sample introducing tube 22 before the filtration device 1, and perform filtration while heating the sample introducing tube 22.

After sampling is completed, the hollow fiber membrane 3 is cut in a longitudinal direction by a razor or the like, and the inner surface on which the fine particles in the ultrapure water are trapped is exposed. When the exposed inner surface is observed with an optical microscope, the fine particles on the membrane are dyed with a fuchsin-methylene blue stain solution, and when they are observed with a scanning electron microscope, sputtering treatment is performed. After the above pretreatment is performed, the inner surface is magnified by the optical microscope or the scanning electron microscope, and the number of fine particles within a counting field is counted. With the above microscope, about 0.01% of an effective filtration area is actually observed by moving a field of view to count the number of trapped fine particles, and the number of fine particles in the ultrapure water per unit volume is calculated by the following formula (particle number concentration calculation formula).

[Formula 1]

$$N = \left(\frac{N_s}{n_s} - \frac{N_b}{n_b}\right) \times \frac{A}{a} \times \frac{1}{V_s - V_b} \quad (1)$$

N: number of fine particles per 1 ml of ultrapure water (particles/ml)
$N_s$: number of fine particles within the counting field (particles)
$N_b$: number of fine particles within the counting field in a blank test (particles)
$n_s$: number of counting fields
$n_b$: number of fields of view in the blank test
A: effective filtration area (mm$^2$)
a: area of one field of view (mm$^2$)
$V_s$: filtration capacity (ml)
$V_b$: filtration capacity in the blank test (ml)

Second Embodiment

A second embodiment of the present invention will be described. A filtration device for measuring the number of fine particles is a hollow fiber membrane module including a hollow fiber membrane unit constituted by liquid-tightly bonding and fixing a hollow membrane to an easily detachable joint (fixing member) with an adhesive (resin mold part). As examples of the easily detachable joint (fixing member), screwed joints such as a commercially available nipple, socket, union, and bushing are mentioned. Depending on the situation, a workpiece produced by cutting a round bar or the like and adding any screw or a ferrule joint is also available. As examples of the material for the joint (fixing member), stainless steel and plastics such as a polyvinyl chloride resin, a polyvinylidene fluoride resin, a polyethylene resin, and a polypropylene resin are mentioned depending on sampling points. Particularly, for example, the stainless steel, polyvinylidene fluoride resin, and so on are preferable because of their good pressure resistance and heat resistance characteristics.

As examples of the adhesive with which the hollow fiber membrane is fixed to the joint (fixing member), an epoxy resin, an urethane resin, a silicone resin, and so on are mentioned in terms of pressure resistance and heat resistance characteristics.

The structure of the hollow fiber membrane module (filtration device for measuring the number of fine particles) may be a one-end open structure in which one end opening on one side of a hollow fiber membrane flux is sealed with the adhesive or may be a both-end open structure in which both sides are open. Note, however, that in the case of the both-end open structure, all of the ultrapure water is filtrated, so that it is necessary to add a valve or the like on one side of the hollow fiber membrane module, but flushing and rinsing can be easily performed.

As examples of a method of liquid-tightly bonding and fixing the hollow fiber membrane to the joint (fixing member), a method of putting a necessary number of linear hollow fiber membranes into the joint (fixing member) and fixing them with the adhesive, a method of making a hole larger than the membrane diameter of the hollow fiber membrane in the joint (fixing member) and inserting the hollow fiber membrane therein and fixing it with the adhesive, and so on are mentioned.

Figure 3:
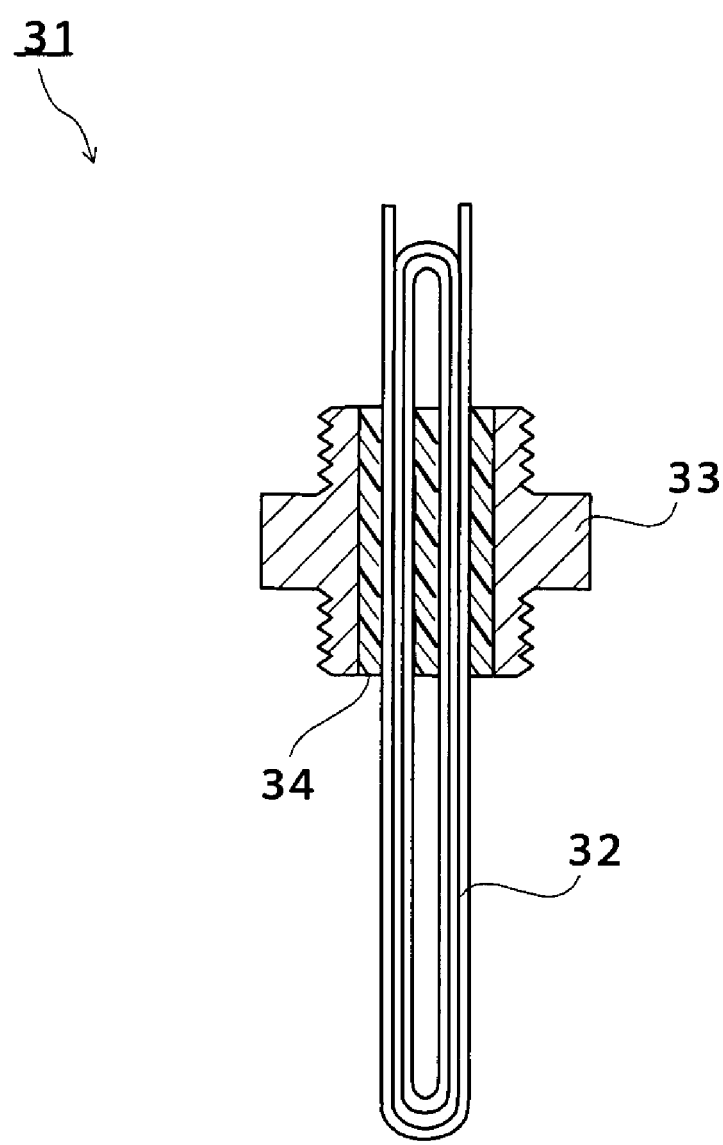
FIG. 3 is a sectional view showing the constitution of a filtration device for measuring the number of fine particles in ultrapure water according to a second embodiment.

Further, when there is a long linear hollow fiber membrane, by fixing it to the joint (fixing member) by a method shown below, a filtration device for measuring the number of fine particles 31 such as shown in FIG. 3 can also be fabricated. First, one long linear hollow fiber membrane 32 is prepared and plural rings are formed by bending the hollow fiber membrane 32 in a O-shape so that the rings lie on top of one another. The hollow fiber membrane 32 is passed through the joint 33 (fixing member) in this state and fixed with an adhesive 34. When in use, a side (upper side in FIG. 3) from which the ultrapure water is introduced is cut. For example, when a ring is formed twice, if the side from which the ultrapure water is introduced of the hollow fiber membrane 32 is cut when in use, six open end portions of the hollow fiber membrane 32 come to converge. According to this method, the follow fiber membrane 32 can be easily fixed, and further very few contamination fine particles adhere to the inner surface since only two portions, that is, both ends are open until just before use. Incidentally, it is desirable to seal both ends of the hollow fiber membrane 32 with the adhesive until just before use to more effectively prevent the adhesion of the contamination fine particles to the inner surface thereof.

Third Embodiment

Figure 4:
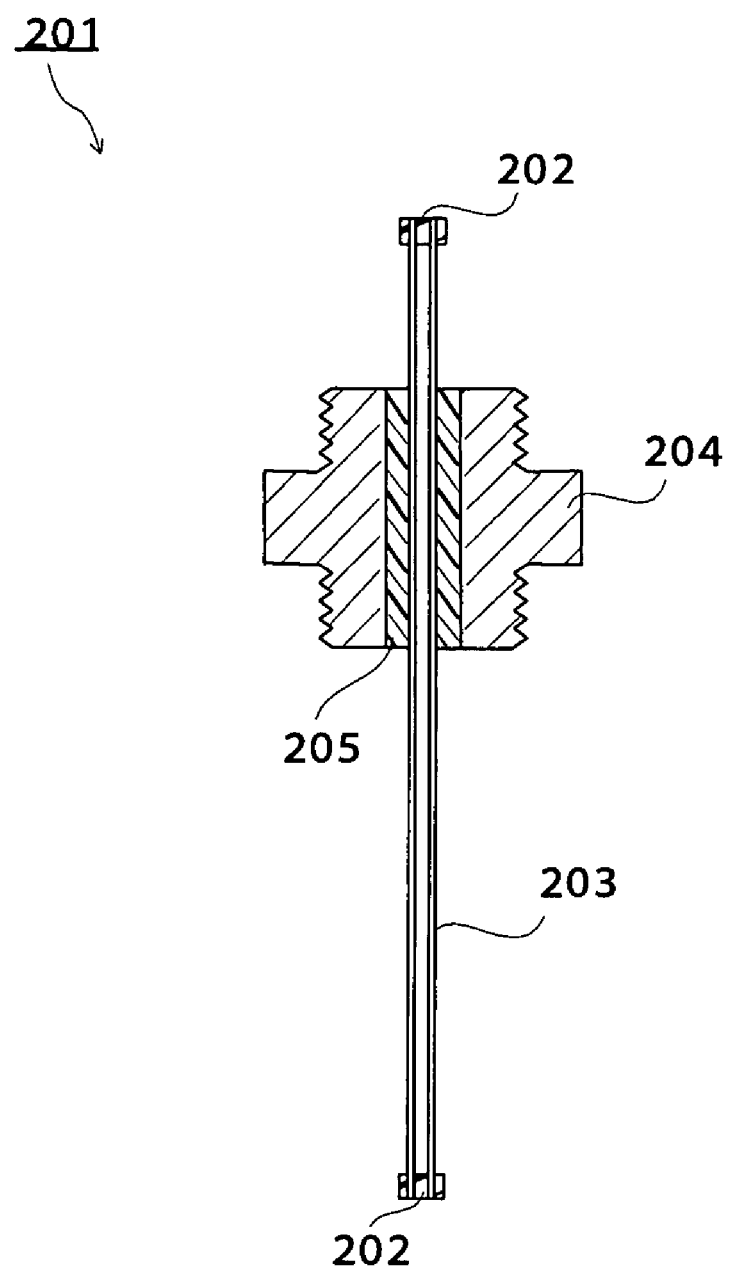
FIG. 4 is a sectional view showing the constitution of a hollow fiber membrane unit for use in a filtration device for measuring the number of fine particles in ultrapure water according to a third embodiment.

A third embodiment of the present invention will be described with reference to FIG. 4. FIG. 4 is a sectional view showing the constitution of a hollow fiber membrane unit for use in a filtration device for measuring the number of fine particles according to the third embodiment.

A hollow fiber membrane unit 201 includes a hollow fiber membrane 203 with both ends sealed with a sealing resin 202 (adhesive). Further, the hollow fiber membrane unit 201 is bonded and fixed to a fixing member such as a nipple 204 with an adhesive 205 (resin mold part) such as an epoxy resin while sealed portions at both ends are exposed. By previously sealing both ends of the hollow fiber membrane 203 with the sealing resin 202 or the like as just described, an inner surface being a surface on which fine particles are trapped can be maintained in a clean state until before use. Incidentally, the number of hollow fiber membranes 203 is not particularly limited, and may be a single number or a plural number.

When in use, the filtration device is fabricated by loading a holder (external cylinder) with this hollow fiber membrane unit 201 and cutting either one (a side from which the ultrapure water is introduced into the hollow fiber membrane) of the sealed portions at both ends to allow the hollow fiber membrane 203 to open.

Fourth Embodiment

Figure 5:
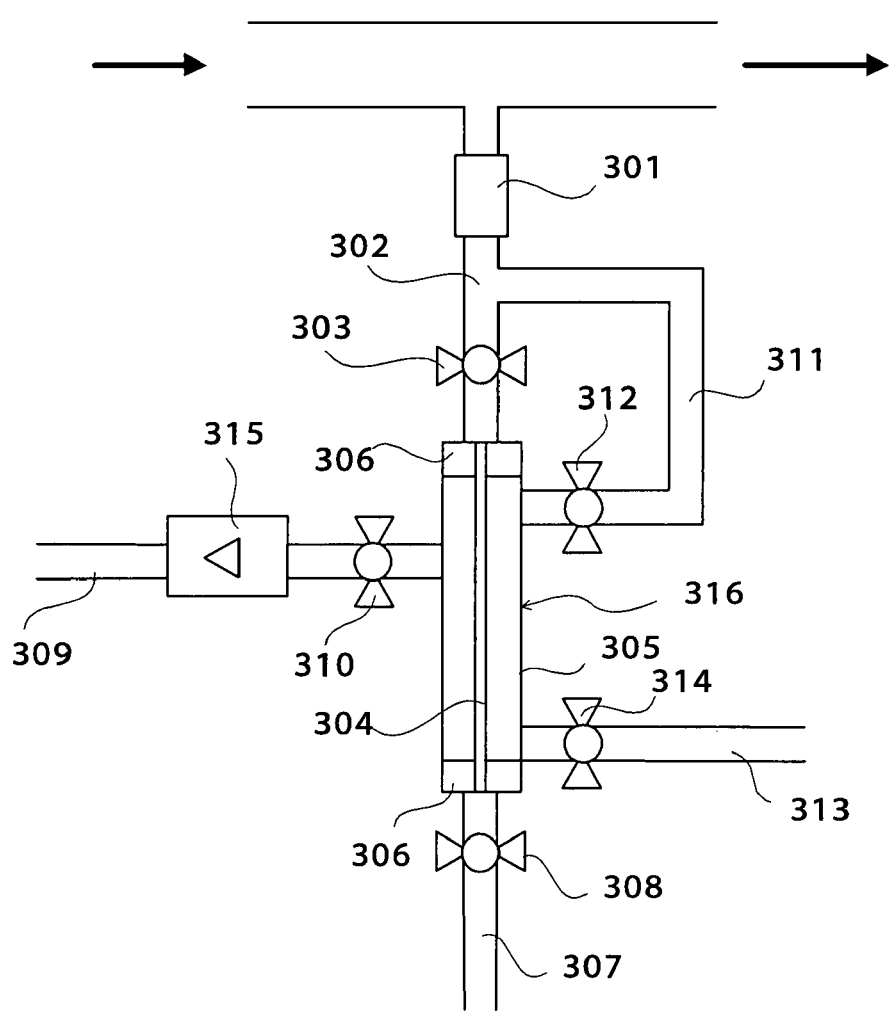
FIG. 5 is a schematic diagram showing a method for measuring the number of fine particles in ultrapure water according to a fourth embodiment.

A fourth embodiment of the present invention will be described with reference to FIG. 5. FIG. 5 is s schematic diagram showing a method for measuring the number of fine particles in ultrapure water according to the fourth embodiment.

As shown in FIG. 5, a connecting jig 301 connected to a sampling port of an ultrapure water production system, a feed-water line 302 of the ultrapure water branching off from a pipe through which the ultrapure water flows from the ultrapure water production system to a point of use, a supply valve 303, a hollow fiber membrane 304, a housing 305 (external cylinder), an adhesive 306 to fix the hollow fiber membrane, a concentrated water line 307, a concentration valve 308, a filtered water line 309, a filtration valve 310, a blow water supply line 311, a blow water supply valve 312, a blow water discharge line 313, a blow water discharge valve 314, a means for measuring an integrated filtration volume (filtration volume), and a filtration device for measuring the number of fine particles 316 are provided. Incidentally, the number of hollow fiber membranes 304 mounted in the filtration device 316 may be a single number or a plural number, but five or more is preferable to improve the analytical precision.

First, before sampling is started, the sampling port of the ultrapure water production system is fully subjected to blowing, and connection to the sampling port by the connecting jig 301 is performed. Then, the concentration valve 308 and the blow water discharge valve 314 are opened and the blow water supply valve 312 is slowly opened to perform a certain amount of substitution in the filtration device 316. Subsequently, the blow water supply valve 312 is slowly closed, and the concentration valve 308 and the blow water discharge valve 314 are closed. Thereafter, by opening the filtration valve 310 and slowly opening the supply valve 303, the ultrapure water containing fine particles is supplied to the hollow fiber membrane 304 in the filtration device 316 via the connecting jig 301, the feed-water line 302 of the ultrapure water, and the supply valve 303 by water pressure of the sampling port of the ultrapure water production system.

The ultrapure water is screen-filtered through the hollow fiber membrane 304 by water pressure and the fine particles in the ultrapure water are trapped by a skin layer on an inner surface. The ultrapure water from which the fine particles are removed is supplied to the means 315 for measuring the integrated filtration volume (filtration volume) via the filtered water line 309 and the filtration valve 310, and the integrated filtration volume (filtration volume) is measured. After a predetermined integrated filtration volume (filtration volume) is obtained, the supply valve 303 is closed and the filtration valve 310 is closed to complete the sampling. After the completion of the sampling, the filtration device 316 is hermetically sealed by closing five valves 303, 308, 310, 312, and 314, and the adhesion of contamination fine particles from an atmosphere to the hollow fiber membrane 304 (fine particle contamination) is completely prevented. When the hollow fiber membrane 304 is taken out of the filtration device 316, holdup liquid remaining in the hollow fiber membrane 304 contains a high concentration of fine particles. Therefore, the fine particles in the holdup liquid are prevented from flowing out by using a method of opening the filtration valve 310 and drying it at room temperature or high temperature (equal to or lower than an upper limit working temperature of each of various members), a method of pushing it out to the filtration side by clean $N_2$ gas or the like without fine particle contamination which has been transmitted through an air filter, or using both these methods.

Then, the hollow fiber membrane 304 is taken out of the filtration device 316 in a clean environment such as a clean bench (clean room). After this, a sample is created according to an instrument which counts the number of trapped fine particles in consideration of apparatus used and the like to prevent the adhesion of contamination fine particles (fine particle contamination), and the number of fine particles on the surface of the skin layer of the hollow fiber membrane is counted by the measuring instrument. Subsequently, the number of fine particles in the ultrapure water is calculated from the integrated filtration volume (filtration volume), skin layer area (effective filtration area), observed field area (area of one field of view), number of observed fields (number of counting fields), and so on. Incidentally, each of constituent units and members used in the filtration device 316 need to be of a structure, a material, and a grade without the adhesion of contamination fine particles (fine particle contamination). Particularly, members commercially available specifically for the ultrapure water are preferable. As for a method for counting the number of fine particles on the surface of the skin layer, according to the particle diameter as a measuring object, the number is measured, for example, using an optical microscope, a scanning electron microscope, or a surface inspection apparatus by a laser light scattering method, or using them together. In particular, a method capable of high magnification, wide field of view, and automatic counting is preferable. Further, the holdup liquid remaining in the device 316 after the sampling is completed is only a small fraction of the whole filtration volume, so that it may be excluded from the above integrated filtration volume.

Fifth Embodiment

Figure 6:
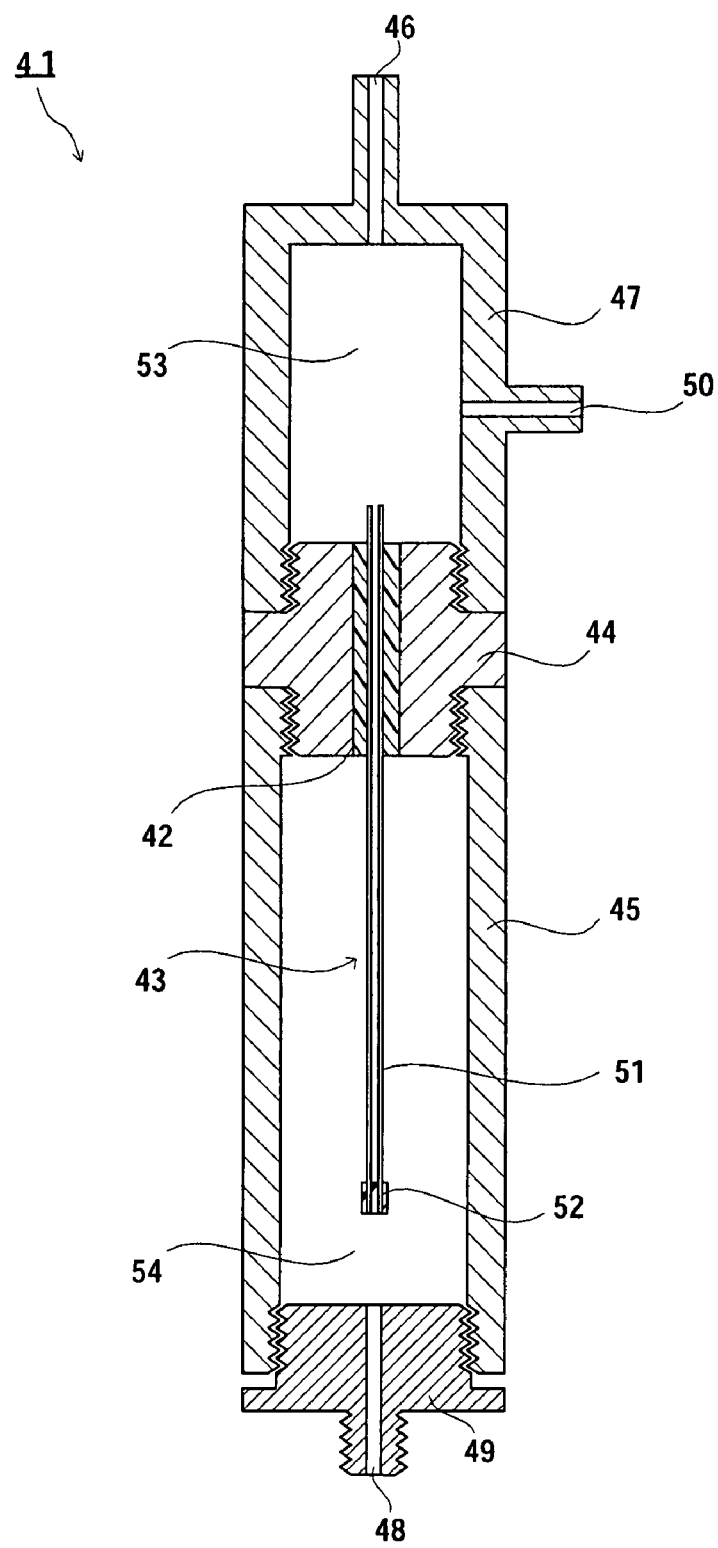
FIG. 6 is a sectional view showing the constitution of a filtration device for measuring the number of fine particles according to a fifth embodiment.
Figure 7:
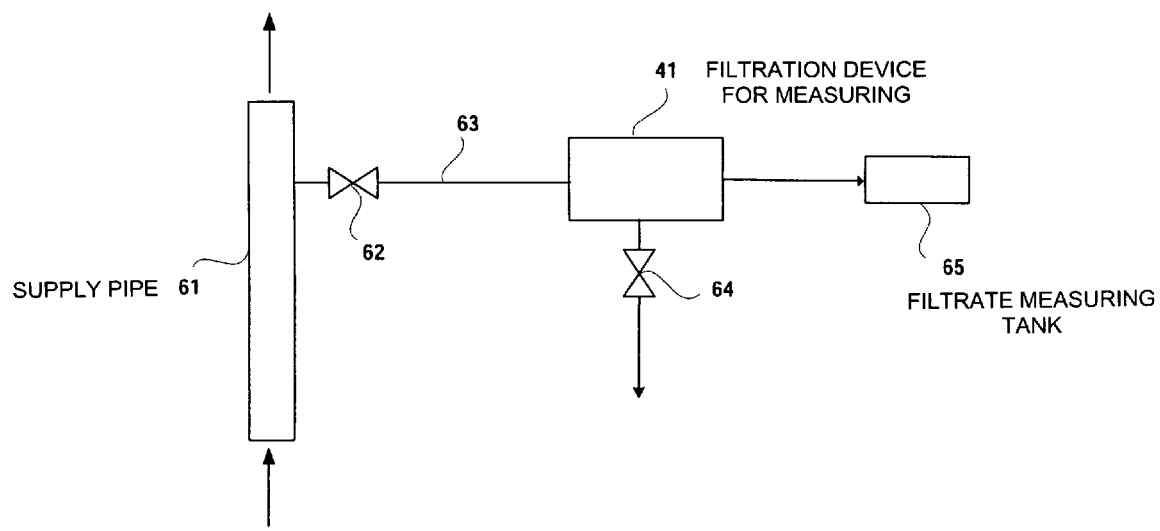
FIG. 7 is a schematic diagram showing an example of a method for measuring the number of fine particles in ultrapure water using the filtration device for measuring the number of fine particles shown in FIG. 6.

A fifth embodiment of the present invention will be described with reference to FIG. 6 and FIG. 7. FIG. 6 is a sectional view showing the constitution of a filtration device for measuring the number of fine particles according to this embodiment. FIG. 7 is a schematic view showing an example of a method for measuring the number of fine particles in ultrapure water using the filtration device for measuring the number of fine particles shown in FIG. 6.

A filtration device for measuring the number of fine particles 41 includes a hollow fiber membrane unit 43. The hollow fiber membrane unit 43 includes a hollow fiber membrane 51, one end portion of the hollow fiber membrane 51 is sealed with a sealing resin 52 (adhesive), and the other end portion thereof is in an open state. Further, a fixing member such as a nipple 44 is fixed to the hollow fiber membrane unit 43 via a resin mold part 42 (adhesive) such as an epoxy resin provided between the sealed portion and the open portion of the hollow fiber membrane 51. A water drain part external cylinder 45 is connected to this nipple 44. The water drain part external cylinder 45 functions as a casing of the hollow fiber membrane 51, and a water drain part joint 49 having a water drain port 48 is connected to the water drain part external cylinder 45. Further, a water supply part external cylinder 47 having a water supply port 46 is connected to the other side of the nipple 44, and a blow water drain port 50 through which the ultrapure water is drained to the outside of the device 41 when the ultrapure water is supplied from the water supply port 46 side is provided in the water supply part external cylinder 47.

The above hollow fiber membrane unit 43, water drain part external cylinder 45, water supply part external cylinder 47, and water drain part joint 49 can be respectively removably attached. These members are fitted to each other, for example, by a screw structure fitting method, and the sealing performance in the device 41 is ensured in portions other than the water supply port 46 and the blow water drain port 50 of the water supply part external cylinder 47 and the water drain port 48 of the water drain part joint 49. Materials for the water drain part external cylinder 45, the water supply part external cylinder 47, and the water drain part joint 49 are only required not to produce dust and not to be eluted, and synthetic resins such as PVDF (polyvinylidene fluoride), PFA (tetrafluoroethylene-perfluoroalkylvinyl ether copolymer), PEEK (polyetheretherketone), are examples thereof.

The filtration device for measuring the number of fine particles 41 is divided into an upstream 53 which communicates with the inner surface side of the hollow fiber membrane 51 via the open end of the hollow fiber membrane 51 and a downstream 54 which touches the outer surface side of the hollow fiber membrane 51 by the nipple 44 or the like. The movement of fine particles and the like in the ultrapure water between the upstream 53 and the downstream 54 is performed only via the membrane surface of the hollow fiber membrane 51.

Incidentally, in FIG. 6, the hollow fiber membrane 51 is fixed with one end sealed and the other end portion open, but the fixing method of the hollow fiber membrane 51 is not limited to this, and, for example, the hollow fiber membrane 51 may be fixed with an adhesive such as resin while being bent in a U-shape. The hollow fiber membrane unit 43 is provided at one end edge of the water drain part external cylinder 45, but, for example, it may be mounted therein while being in close contact with an inner wall of the external cylinder 45. Further, in FIG. 6, the water supply port 46 and the blow water drain port 50 are provided in the water supply part external cylinder 47, and it is desirable to provide two or more of such ultrapure water supply/drain ports. The water drain part joint 49 having the water drain port 48 is connected to the water drain part external cylinder 45, and it is desirable to provide one or more of such ultrapure water supply/drain ports.

Next, an example of a manufacturing method of the filtration device for measuring the number of fine particles of this embodiment will be described using FIG. 6.

First, to prevent the inner surface side of the hollow fiber membrane 51 on which the fine particles in the ultrapure water are trapped from being contaminated from outside, both ends of the hollow fiber membrane 51 are sealed with the epoxy resin or the like. The number of hollow fiber membranes 51 is preferably one to 10, and the length of the follow fiber membrane 51 is preferably 30 mm to 100 mm at the completion of assembly of the filtration device 41.

The hollow fiber membrane unit 43 is fabricated by passing the hollow fiber membrane 51 with both ends sealed through the nipple 44 made of SUS (Steel Use Stainless: stainless steel) or PEEK or the like and closely fixing the hollow fiber membrane 51 and the nipple 44 by the epoxy resin or the like. At this time, there is a high possibility that contamination fine particles adhere to the fixing member such as the nipple 44, which becomes a factor of measurement errors in sampling, and hence, washing treatment by ultrasonic irradiation or the like is performed in advance. As examples of a washing method, in addition to the ultrasonic irradiation, ethanol immersion, surfactant washing, ultrapure washing, and so on are mentioned.

Then, the fabricated hollow fiber membrane unit 43 is subjected to hydrophilic treatment. The hydrophilic treatment makes it possible to recover the water permeability which lowers as the hollow fiber membrane 51 becomes drier. Further, the hollow fiber membrane 51 has innumerable pores, and microscopically its membrane surface has a great many irregularities. In many cases, blank particles (contamination fine particles) stick to the pores, gaps between irregularities, and the interiors of the pores, which are resistant to getting wet in water, so that it is desirable to remove the blank particles (contamination fine particles) sticking to the above portions by allowing a medical agent or hot purewater with a hydrophilic action to permeate the above portions. As examples of a method for making it hydrophilic, a method of immersing it in pure water or a medical agent at 40° C. or higher for 0.5 hours to 12 hours and preferably for one hour to four hours, a method of passing pure water therethrough at 25° C. or higher under pressure, and so on are mentioned. In immersing it in the pure water or the medical agent, to improve the effect of removing the blank particles (contamination fine particles), ultrasonic waves, warming, or the like may be further combined therewith. The frequency of ultrasonic waves is not particularly limited, but ultrasonic waves with a frequency from 0.8 MHz to 3 MHz are preferable, which can obtain the higher effect of removing the blank particles (contamination fine particles). Meanwhile, in the case of warming, to improve the effect of removing the blank particles (contamination fine particles), 40° C. to 80° C. is preferable. The above medical agent is only required to exhibit the hydrophilic action without exerting influences such as a reduction in the membrane performance and degradation on the hollow fiber membrane 51, and, alcohol, a surfactant, and the like are mentioned as examples thereof. When the alcohol is used, its type is not particularly limited, but methanol, ethanol, isopropanol, or a mixture thereof can be preferably used. When the surfactant is used, its type is not particularly limited, but an anionic surfactant, a cationic surfactant, a nonionic surfactant, or an amphoteric surfactant can be preferably used. Its concentration is preferably 0.1% to 5%, and more preferably 0.1% to 1%. Incidentally, when used with its concentration adjusted, ultrapure water containing the same or smaller number of fine particles as/than that of the ultrapure water as the measuring object is used.

After the hydrophilic treatment, push water is filled in the downstream 54 of the filtration device 41 formed by fitting the water drain part joint 49 into the water drain part external cylinder 45, the hollow fiber membrane unit 43 subjected to the hydrophilic treatment is mounted, and further the push water is supplied to the water drain port 48 of the water drain part joint 49 to perform backwashing. At this time, concerning downstream members such as the water drain part external cylinder 45 and the water drain part joint 49, contamination fine particles are previously subjected to washing treatment by ultrasonic irradiation or the like. As the push water, an antibacterial agent having at least a bactericidal effect and/or an antibacterial effect, that is, a medical agent which inhibits the growth of bacteria can be used, and it is recommended to further have an effect of improving hydrophilicity. The antibacterial agent is only required to exhibit the antibacterial action without exerting influences such as a reduction in the membrane performance and degradation on the hollow fiber membrane 51, and alcohol, a reductant, and the like are mentioned as examples thereof. When the alcohol is used, its type is not particularly limited, but methanol, ethanol, isopropanol, or a mixture thereof can be preferably used. When the reductant is used, its type is not particularly limited, but, for example, sodium sulfite, sodium hydrogen sulfite, or the like can be used. Its concentration is preferably 0.1% to 10%, and more preferably 0.1% to 1%. After bleeding of the antibacterial agent from the upstream of the hollow fiber membrane 51 is confirmed in a backwash process by the antibacterial agent, one end of the above hollow fiber membrane 51 is cut and opened by a clean razor, and the water supply part external cylinder 47 from which contamination fine particles are previously removed is attached while the antibacterial agent continues to be reversely passed. As a backwash pressure by the antibacterial agent, 0.5 kgf/cm$_2$ to 3 kgf/cm$_2$ is preferable, and 1 kgf/cm$_2$ to 2 kgf/cm$_2$ is more preferable. At this time, until the antibacterial agent overflows the water supply port 46 of the water supply part external cylinder 47, it is reversely passed. After release of air from within the hollow fiber membrane 51 is confirmed, the device is brought into a sealed state with the water drain port 48 and the water supply port 46 capped while the antibacterial agent is filled therein. By assembling the fine particle trapping device 41 while the antibacterial agent is reversely passed through the hollow fiber membrane 51 as just described, the adhesion of the contamination fine particles on the inner surface side of the hollow fiber membrane 51 and into the device 41 and multiplication of microorganisms can be avoided, and high cleanliness can be maintained. Further, when the hollow fiber membrane 51 is stored and carried, there is a possibility that the hollow fiber membrane 51 is contaminated from outside, but since the device 41 is stored and carried while the antibacterial agent is adhering to the surface of the hollow fiber membrane 51, the adhesion of contamination fine particles to the hollow fiber membrane 51 can be avoided. Accordingly, by backwashing the hollow fiber membrane 51 using the antibacterial agent, not only the blank particles (contamination fine particles) can be effectively removed but also the adhesion of contamination fine particles to the hollow fiber particle 51, multiplication of microorganisms, and so on can be prevented.

Next, an example of a method for measuring the number of fine particles in ultrapure water of this embodiment will be described using FIG. 7. FIG. 7 is a schematic diagram showing the method of measuring the number of fine particles in the ultrapure water of this embodiment using the filtration device shown in FIG. 6.

First, the ultrapure water is reversely passed from a sampling valve 62 attached to a supply pipe 61 of an ultrapure water production system being an inspection object through a sample introducing tube 63 using the pressure of the supply pipe 61 from the water drain part joint 49 of the filtration device 41 into which the antibacterial agent is filled. The backwash time is preferably one minute to 60 minutes, and more preferably five minutes to 20 minutes. By performing backwashing from the outer surface side to the inner surface side of the hollow fiber membrane 51 using the ultrapure water, the antibacterial agent filled into the filtration device 41 is discharged and substituted by the ultrapure water, and also the washing effect on the inner surface side of the hollow fiber membrane 51 can be improved.

After the backwashing by the ultrapure water, the water drain part joint 49 is capped, a flow regulating valve 64 is attached to the blow water drain port 50 of the water supply part external cylinder 47, and the ultrapure water is supplied to the water supply port 46 and discharged toward the blow water drain port 50. Hence, fine particles (contamination fine particles) which have adhered when the filtration device 41 was installed can be removed. At this time, the flow rate (blow rate) is 200 ml/min or more, and particularly preferably 300 ml/min to 600 ml/min. Further, the water-passing time is preferably five minutes or more.

Then, sampling of the ultrapure water is performed. Namely, the ultrapure water is passed through the filtration device 41 loaded with the hollow fiber membrane unit 43 to be subjected to internal pressure filtration, and fine particles in the ultrapure water are trapped on the inner surface of the hollow fiber membrane 51. At this time, it is desirable to regulate the blow rate by the flow regulating valve 64 attached to the blow water drain port 50, and set the ratio (flow ratio) between the above blow rate and the filtration flow rate to 3:1 to 100:1, and particularly to 20:1 to 50:1. The fine particles in the ultrapure water are trapped on the inner surface of the hollow fiber membrane 51 of the filtration device 41, and the ultrawater is passed until a given water volume is stored in a filtrate measuring tank 65. The filtrate measuring tank 65 is a measuring tank as a measuring means, and as the measuring means, any one which can measure a given filtration volume is available, and as examples thereof, in addition to the measuring tank, a flow integrator and so on are mentioned. Incidentally, a pressuring means by a pump or gas or the like may be provided in the supply pipe 61 if necessary. By using the pressurizing means, the filtration velocity can be increased, and the filtration time can be further shortened. Further, it is also possible to provide a heating means such as a heater in the supply pipe 61 and perform filtration while warming the ultrapure water at a maximum temperature of 80° C. or less by heating the supply pipe 61.

After the sampling is completed, the hollow fiber membrane 51 is cut in a longitudinal direction by a razor or the like, and the inner surface side on which the fine particles in the ultrapure water are trapped is exposed. When the exposed inner surface side is observed with an optical microscope, the fine particles on the membrane are dyed with a fuchsin-methylene blue stain solution, and when it is observed with a scanning electron microscope, sputtering treatment is performed.

After the above pretreatment is performed, the inner surface side is magnified by the optical microscope or the scanning electron microscope, and the number of fine particles within a counting field is counted. With the above microscope, about 0.01% of an effective filtration area is actually observed by moving a field of view to count the number of trapped fine particles, and the number of fine particles in the ultrapure water per unit volume is calculated by the above formula (1).

Hereinafter, the present invention will be specifically described with examples, but the present invention is not limited to the examples.

Example 1, Comparative Examples 1, 2

The number of fine particles in the ultrapure water is measured using the filtration device for measuring the number of fine particles 1 shown in FIG. 1. First, six hollow fiber membranes 3 (OLT5026 manufactured by Asahi Kasei Corporation) made of polysulfone each having an inner diameter of 0.6 mm, an outer diameter of 1.1 mm, a length of 3 cm, and an effective membrane area of 3.1 cm² are bundled and fixed to the nipple 5 with the adhesive 2 (epoxy resin). After this, the filtration device 1 shown in FIG. 1 is fabricated by housing the six hollow fiber membranes 3 in the water drain part external cylinder 4 (holder) and connecting the water supply part external cylinder 6 and the water drain part joint 7 thereto, respectively. Then, the ultrapure water is directly introduced into the filtration device 1 from the sampling valve attached to the sample introducing tube of the ultrapure water production system, and internal pressure filtration is performed under conditions of a filtration pressure of 0.2 MPa and 25° C. After sampling is completed, the hollow fiber membrane 3 is taken out, cut in the longitudinal direction by a razor to expose the inner surface thereof, and subjected to sputtering. Then, the number of fine particles on the inner surface of the hollow fiber membrane 3 is observed at 20,000-fold magnification with the scanning electron microscope, and the number of fine particles adhering to the inner surface of the hollow fiber membrane 3 within the counting field is counted. With the measuring object as a fine particle with a particle diameter of 0.02 μm or more, the number of days of filtration as 10 days, and the number of counting fields as 1000 fields, the number of blank particles (number of contamination fine particles), value of countable fine particles, number of counting fields, counting field area, filtration volume, and so on are counted and shown in Table 1. As a result of calculating the number of fine particles contained in 1 ml of ultrapure water, the number of fine particles in 1 ml of ultrapure water (particle number concentration) is 5 particles/ml.

As comparative examples, an MF membrane as a flat membrane made of polycarbonate with a pore diameter of 0.03 μm (Comparative Example 1) and an UF membrane as a flat membrane made of regenerated cellulose (Comparative Example 2) are used.

The MF membrane as the flat membrane used as Comparative Example 1 is unsuitable for the present invention since its pore diameter is larger than the fine particle as the measuring object.

The UF membrane as the flat membrane used as Comparative Example 2 is unsuitable for the present invention since it is estimated that the required filtration water volume and number of days of filtration making the fine particle number concentration of 0.02 μm or more as the measurement result of Example 1 to be 5 particles/ml become enormous.

A method for calculating the estimated calculated values of the filtration water volume and the number of days of filtration will be shown below. First, for sake of simplicity, the filtration volume $V_b$ in the blank test is assumed to be 0. The number of counting fields of the filtration membrane and the number of counting fields in the black test are set to the same 300 fields. The number of particles required to calculate the particle number concentration is the same as the number of blank particles (number of contamination fine particles). Namely, the value of countable fine particles (containing blank particles) on the filtration membrane becomes twice the number of blank particles (number of contamination fine particles). As a result of substituting N=5, $N_s=N_b\times2=1000$, $N_b=500$, $n_s=n_b=300$, A=314 mm², a=0.0000332 mm² into the above formula (1), the filtration volume $V_s$ is 3150 L. As a result of calculating the number of days of filtration by dividing this filtration volume by a filtration volume per day calculated from the filtration flux, the effective filtration area, and so on, the number of days of filtration is about 280 days.

Example 2, Comparative Examples 3, 4

Example 2 is performed in the same manner as Example 1 except that the measuring object is a fine particle with a particle diameter of 0.03 μm or more, the number of days of filtration is 10 days, and the number of counting fields is 1000 fields. The number of blank particles (number of contamination fine particles), value of countable fine particles, number of counting fields, counting field area, filtration volume, and so on are counted and shown in Table 2. As a result of calculating the number of fine particles contained in 1 ml of ultrapure water, the number of fine particles in 1 ml of ultrapure water (particle number concentration) is 3 particles/ml. Further, when the number of counting fields is set to 300 fields in the same hollow fiber membrane, the number of trapped particles is less than the number of particles required to calculate the particle number concentration, so that by substituting the number of fine particles required to calculate the particle number concentration into Formula (1), the number of fine particles in 1 ml of ultrapure water (fine particle number concentration) is calculated, and the representation of a result is shown as less than this value in Table 2.

A method for calculating the fine particle number concentration will be shown below. The number of fine particles required to calculate the fine particle number concentration is 20 at the minimum, and the number of trapped particles subjected to correction by blank particles is less than this value.

Value of countable fine particles (containing blank particles)=7

Number of blank particles (number of contamination fine particles)=1

Number of trapped particles=7−1=6<20

Hence, the number of trapped particles is assumed to be 20 particles and substituted into Formula 1, and the result is defined as less than the obtained fine particle concentration. Consequently, in 300 counting fields, the particle number concentration becomes less than 8 particles/ml. From the above, in Example 2, since the number of blank particles (number of contamination fine particles) of this hollow fiber membrane is small, the required number of fine particles (20 particles) can be counted by 1000 counting fields, and the measurement result of 3 particles/ml can be obtained.

Incidentally, as comparative examples, an MF membrane as a flat membrane made of polycarbonate with a pore diameter of 0.03 µm (Comparative Example 3) and an UF membrane as a flat membrane made of regenerated cellulose (Comparative Example 4) are used.

Comparative Example 3 is performed in the same manner as Example 2 using the MF membrane as the flat membrane with the number of days of filtration as 10 days and the number of counting fields as 300 fields, but the number of trapped particles is less than the number of particles required to calculate the particle number concentration. Hence, by substituting the number of fine particles required to calculate the particle number concentration into Formula (1), the number of fine particles in 1 ml of ultrapure water is calculated, and the representation of a result is shown as less than this value in Table 2. As shown in Table 2, the number of blank particles (number of contamination fine particles) adhering to the membrane surface is larger than that in Example 2, so that the merit of increasing the number of counting fields cannot be expected.

Comparative Example 4 is performed in the same manner as Example 2 using the UF membrane as the flat membrane with the number of days of filtration as 10 days and the number of counting fields as 300 fields, but the number of trapped particles is less than the number of particles required to calculate the particle number concentration. Hence, by substituting the number of fine particles required to calculate the particle number concentration into Formula (1), the number of fine particles in 1 ml of ultrapure water is calculated, and the representation of a result is shown as less than this value in Table 2. As shown in Table 2, the number of blank particles (number of contamination fine particles) adhering to the membrane surface is larger than that in Example 2, so that the merit of increasing the number of counting fields cannot be expected.

Example 3, Comparative Examples 5, 6

Example 3 is performed in the same manner as Example 1 except that the measuring object is a fine particle with a particle diameter of 0.03 µm or more, the number of days of filtration is three days, and the number of counting fields is 300 fields. The number of blank particles (number of contamination fine particles), value of countable fine particles, number of counting fields, counting field area, filtration volume, and so on are counted and shown in Table 3. As a result of calculating the number of fine particles contained in 1 ml of ultrapure water, the number of fine particles in 1 ml of ultrapure water is 25 particles/ml.

Incidentally, as comparative examples, an MF membrane as a flat membrane made of polycarbonate with a pore diameter of 0.03 µm (Comparative Example 5) and an UF membrane as a flat membrane made of regenerated cellulose (Comparative Example 6) are used.

Comparative Example 5 is performed in the same manner as Example 3 using the MF membrane as the flat membrane with the number of days of filtration as 28 days and the number of counting fields as 300 fields. The number of blank particles (number of contamination fine particles), value of countable fine particles, number of counting fields, counting field area, filtration volume, and so on are counted and shown in Table 3. As a result of calculating the number of fine particles contained in 1 ml of ultrapure water, the number of fine particles in 1 ml of ultrapure water is 28 particles/ml.

Comparative Example 6 is performed in the same manner as Example 3 using the UF membrane as the flat membrane with the number of days of filtration as 22 days and the number of counting fields as 300 field. The number of blank particles (number of contamination fine particles), value of countable fine particles, number of counting fields, counting field area, filtration volume, and so on are counted and shown in Table 3. As a result of calculating the number of fine particles contained in 1 ml of ultrapure water, the number of fine particles in 1 ml of ultrapure water is 27 particles/ml. As is clear from Tables 1 to 3, in Examples, as compared to Comparative Examples, the number of blank particles (number of contamination fine particles) is smaller, the volume of ultrapure water passing through the filtration membrane when the fine particles are trapped is reduced, and the filtration time is greatly shortened.

Example 4, Comparative Examples 7 to 9

The number of fine particles in the ultrapure water is measured using the filtration device for measuring the number of fine particles 41 shown in FIG. 6. First, one UF hollow fiber membrane (OLT5026 manufactured by Asahi Kasei Corporation) made of polysulfone with an inner diameter of 0.6 mm, an outer diameter of 1.1 mm, a length of 50 mm, and an effective membrane area of 94 mm$^2$ is inserted into the ⅛SUS nipple 44 and fixed with the resin mold part 42 (epoxy resin). Further, the hollow fiber membrane unit with both ends sealed is fabricated by sealing both ends of the follow fiber membrane with the epoxy resin. The hollow fiber membrane unit with both ends sealed is immersed in a surfactant and made hydrophilic.

After this, sodium hydrogen sulfite is filled into the downstream members constituted by connecting the water drain part external cylinder 45 and the water drain part joint 49, and the hollow fiber membrane unit with both ends sealed which has been made hydrophilic is inserted. The sodium hydrogen sulfite is supplied from the water drain part joint 49. After it is confirmed that the sodium hydrogen sulfite bleeds from the upper portion of the hollow fiber membrane, the upper portion (5 mm to 10 mm higher than the nipple 44) of the hollow fiber membrane is cut by a clean razor. Further, the sodium hydrogen sulfite is reversely passed to release air in the hollow fiber membrane. Subsequently, while the sodium hydrogen sulfite is reversely passed under pressure, the water supply part external cylinder 47 is attached. After it is confirmed that the sodium hydrogen sulfite overflows the water supply port 46 of the water supply part external cylinder 47, the supply port 46 is capped. The water drain port 48 of the water drain joint 49 is capped, and thereby the filtration device 41 is brought into a sealed state.

Then, the ultrapure water is introduced into the filtration device 41 shown in FIG. 6 through the clean sample introducing tube from the sampling valve attached to the pipe of the ultrapure water production system as the inspection object. The sampling valve used here is sterilized by hot pure water and subjected to blowing for 12 hours or more just before attachment. The ultrapure water is supplied to the water drain port 48 of the water drain part joint 49, the sodium hydrogen sulfite filled in the device 41 is discharged by reverse passage and substituted by the ultrapure water. Thereafter, the water drain port 48 of the water drain joint 49 is capped, and the ultrapure water is supplied to the water supply port 46 of the water supply part external cylinder 47. The flow regulating valve is attached to the blow water drain port 50 of the water supply part external cylinder 47, and blowing is started at 600 ml/min. After blowing for five minutes, the blow volume is regulated to 100 ml/min by the flow regulating valve. After the regulation, the water drain port 48 of the water drain part joint 49 is uncapped.

After this, sampling of the ultrapure water is started, and the ultrapure water is subjected to internal pressure filtration through the UF hollow fiber membrane 51 at a filtration pressure of 0.5 MPa and a temperature of 25° C. The filtration flow rate is 4 ml/min. The ratio between the blow volume of the blow water drain port of the water supply part external cylinder and the filtration flow rate is 25:1. The filtration period is 30 days. After 30 days, the water drain port 48 of the water drain part joint 49 is capped. Thereafter, the flow regulating valve is detached, the blow water drain port 50 is capped, the water supply port 46 of the water supply part external cylinder 47 is capped from the sampling valve, and then the filtration device 41 is carried to the clean room in a sealed state.

In the clean room, the hollow fiber membrane unit 43 is taken out of the device 41, and the hollow fiber membrane 51 is cut in the longitudinal direction by a razor to expose the inner surface thereof and subjected to sputtering. Then, the inner surface of the hollow fiber membrane 51 is observed at 40,000-fold magnification with the scanning electron microscope, and the number of fine particles adhering to the inner surface within the counting field is counted. With the measuring object as a fine particle with a particle diameter of 0.01 μm or more, the filtration period as 30 days, and the number of counting fields as 1200 fields, the number of blank particles (number of contamination fine particles), value of countable fine particles, number of counting fields, filtration volume, and so on are calculated and shown in Table 4. As a result of calculating the number of fine particles contained in 1 ml of ultrapure water, the particle number concentration in 1 ml of ultrapure water is 1 particle/ml.

Incidentally, Comparative Examples 7 to 9 shown below are performed. As Comparative Example 7, sampling of the ultrapure water is performed using the UF membrane as the flat membrane made of regenerated cellulose with the number of days of filtration as 30 days and the number of counting fields as 1200 field. More specifically, filtration is performed using the ultrapure water from the sampling valve attached to the sample introducing tube of the same ultrapure water production system as in Example 4. After the required filtration volume is filtered, the device is carried to the clean room in a sealed state. In the clean room, the flat membrane is subjected to sputtering, and the number of fine particles on the membrane surface is observed at 40,000-fold magnification with the scanning electron microscope, and the number of fine particles adhering to the membrane surface within the counting field is counted. In the same number of days of filtration (30 days) as in Example 4, the number of blank particles (number of contamination fine particles) is larger, and the number of trapped fine particles is less than the number of particles required to calculate the particle number concentration. Therefore, the number of fine particles required to calculate the particle number concentration is assumed to be the number of trapped particles and substituted into the above formula (1) to calculate the number of fine particles in 1 ml of ultrapure water (fine particle number concentration), and the representation of a result is shown as less than this value in Table 4. As shown in Table 4, the fine particle number concentration is less than 20 particles/ml, but the particle number concentration cannot be specified. Next, using the same UF membrane as the flat membrane, the required filtration volume and number of days of filtration for the fine particle number concentration of the measuring object to be 1 particle/ml which is the measurement result of Example 4 are calculated using the above formula (1). As a result, the required filtration volume is 12600 L (provided that 22 L/day), and number of days of filtration is 580 days.

Comparative Example 8 is performed in the same manner as Example 4 except that the blow water drain port 50 of the water supply part external cylinder 47 of the filtration device 41 is not subjected to blowing. When the device 41 is attached to the sampling valve attached to the pipe of the ultrapure water production system, the ultrapure water is not blown from the water supply port 46 to the blow water drain port 50 of the water supply part external cylinder 47, and instead, immediately after the attachment, the water drain port 48 of the water drain part joint 49 is uncapped, and sampling is started. The filtration flux is 4 ml/min. As a result of calculating the number of fine particles contained in 1 ml of ultrapure water, the particle number concentration in 1 ml of ultrapure water is 5 particles/ml.

Comparative Example 9 is performed in the same manner as Example 4 except that the reverse passage of fluid having no antibacterial effect is performed when the filtration device 41 is manufactured. As a result of observing fine particles on the inner surface of the hollow fiber membrane 51 with the scanning electron microscope, counting is impossible due to the growth of visible bacteria.

As is clear from Table 4, in Example 4 using the UF hollow fiber membrane, as compared to Comparative Example 7 using the flat membrane, the number of blank particles (number of contamination fine particles) is smaller, the volume of ultrapure water passing through the filtration membrane when the fine particles are trapped is reduced, and the filtration time can be greatly shortened. Further, in Example 4, by blowing the ultrapure water from the water supply port 46 to the blow water drain port 50 of the water supply part external cylinder 47, fine particle contamination resulting from an introduction system of the filtration device 41 including the sampling valve can be suppressed compared to Comparative Examples 8 and 9.

Example 5

Using the filtration device for measuring the number of fine particles 316 shown in FIG. 5, the number of fine particles of 0.03 μm or more in the ultrapure water is measured.

First, the filtration device for measuring the number of fine particles 316 shown in FIG. 5 is installed at a sampling point of the ultrapure water production system (not shown), and the following sampling is performed. First, to prevent the adhesion of contamination fine particles (fine particle contamination) from a sampling cock of the sampling point, sufficient washing and sterilization are performed. Then, the filtration device for measuring the number of fine particles 316 is attached to the sampling point, the ultrapure water is supplied from a surface (outer surface side in this Example) opposite to a surface on which fine particles are trapped to substitute for filled water in the device 316, and (about 100 ml) of blowing which is approximately 100 times the holdup volume of a flow path space in the hollow fiber membrane 304 and the device 316 is performed. After the blowing is completed, internal pressure dead end filtration is performed at a feed water pressure of 0.5 MPa and an instantaneous filtration volume of approximately 250 ml/Hr/cm² to trap fine particles on the inner surface of the hollow fiber membrane 304. Incidentally, the hollow fiber membrane 304 is an UF hollow fiber membrane (a nominal molecular weight cutoff of 10,000) which is made of polysulfone and manufactured by Asahi Kasei Chemicals Corporation and has a skin layer in each of the inner and outer surfaces. Ten hollow fiber membranes 304 with an outer diameter/inner diameter=1.4 mm/0.6 mm whose total length is regulated so that the effective membrane area per one membrane becomes 1 cm² are mounted in the filtration device for measuring the number of fine particles 316. The integrated filtration volume (filtration capacity) is measured by a commercially available integrating flowmeter.

Meanwhile, prior to the sampling, using a hollow fiber membrane of the same production lot as the hollow fiber membrane 304 used for the sampling and those of plural different lots A to E, the numbers of blank particles (numbers of contamination fine particles) are measured. Results thereof are shown in Table 5.

In this example, a target of the filtration volume is obtained from blank particles (contamination fine particles) of the used hollow fiber membrane and a targeted measurement lower limit. Namely, since the number of fine particles trapped by filtration is acquired from (estimated concentration)×(filtration volume), the filtration volume is determined so that this value greatly exceeds the number of blank particles (number of contamination fine particles) of the hollow fiber membrane. More specifically, it is ideal to trap blank particles, the number of which is approximately 100 times the above number of blank particles, so that to measure the number of fine particles in ultrapure water containing fine particles at a level of 1000 particles/L, approximately 10 L of filtration volume is needed. In this example, since the minimum limit of determination is set to one particle/ml, the total filtration volume required to pass the ultrapure water through 10 hollow fiber membranes is found as 100 L. The time required for the integrated filtration volume to reach the above predetermined filtration volume is about 40 hours, and hence the trapping of fine particles in the ultrapure water is completed in a very short time. The number of fine particles observed on the inner surface of the hollow fiber membrane is shown in Table 6.

A mean value N of the numbers of fine particles trapped on the inner surface of the hollow fiber membrane is found as follows.

$$N = \frac{8.6}{200} \times \frac{100}{6.4 \times 10^{-5}}$$ [Formula 2]
$$= 67187$$

A fine particle concentration C in ultrapure water is calculated by the following equation.

$$C = \frac{N - N_s}{V_s \times 1000}$$

C: fine particle concentration in ultrapure water (particles/ml)
$V_s$: ultrapure water filtration capacity per one hollow fiber membrane (L)
$N_s$: mean value of the numbers of blank particles (numbers of contamination fine particles)

Consequently, the fine particle concentration in the ultrapure water in this example is found as follows.

$$C = \frac{67187 - 1 \times 10^4}{10 \times 1000}$$
$$= 6$$

Further, for measurement at a level of 100 or more particles/L, a reliable measurement result can be obtained if a filtration of 100 L/mm² or more is performed. Incidentally, in this example, also in the case of fine particles of 0.03 μm or less, the same result is obtained, and also in the case of fine particles with a minimal diameter of 0.01 μm or 0.02 μm which are difficult to measure at present, measurement is possible by using a hollow fiber membrane with an appropriate pore diameter.

Example 6

Figure 8:
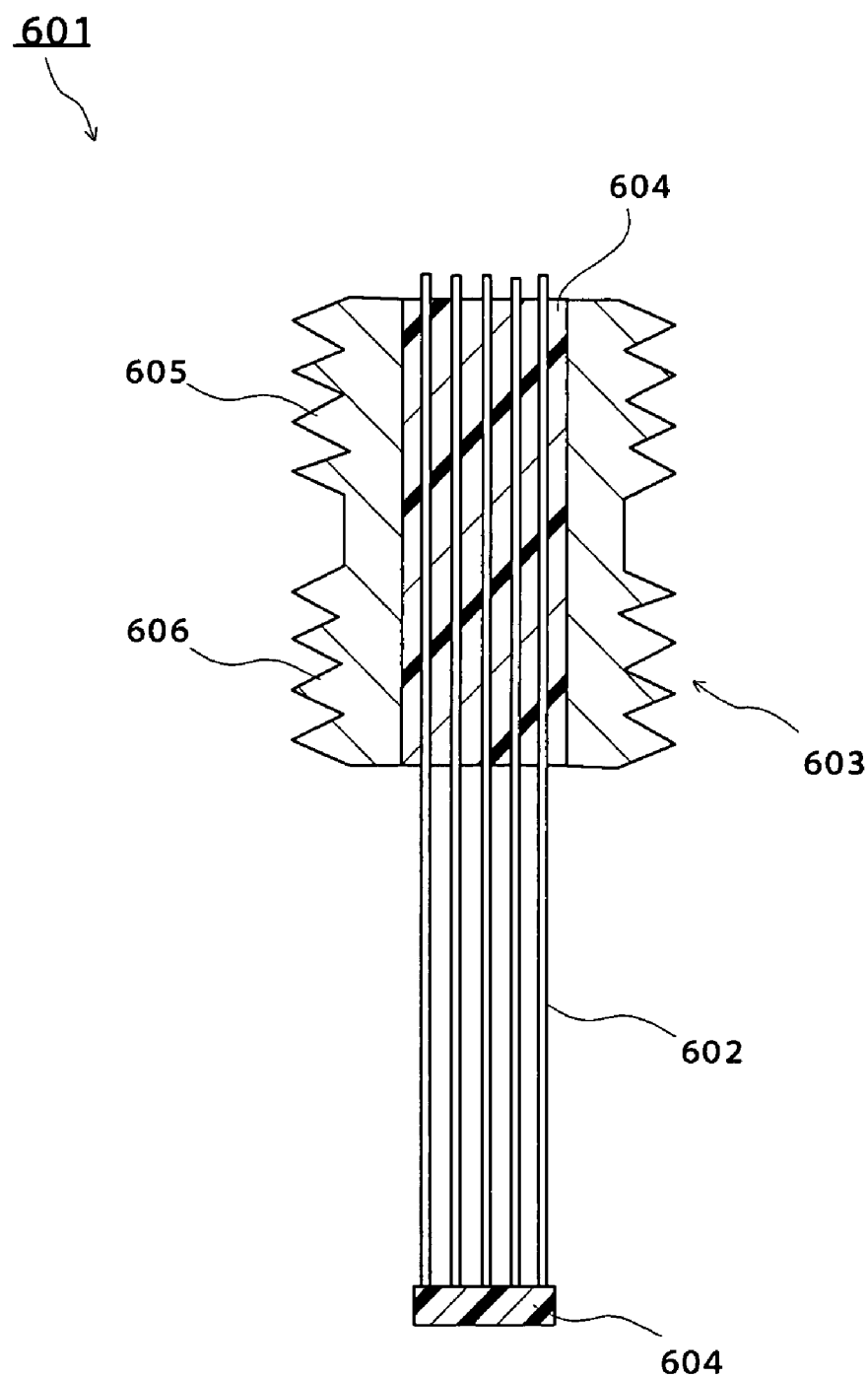
FIG. 8 is a sectional view showing the constitution of a filtration device for measuring the number of fine particles according to Example 6.

The number of fine particles in the ultrapure water is measured using a filtration device for measuring the number of fine particles 601 shown in FIG. 8.

The filtration device for measuring the number of fine particles 601 (hollow fiber membrane module) shown in FIG. 8 and using an UF hollow fiber membrane 602 (a nominal molecular weight cutoff of 10,000, a hollow fiber membrane outer diameter/inner diameter=1.4 mm/0.6 mm) which is made of polysulfone and manufactured by Asahi Kasei Chemicals Corporation and has a skin layer in each of an inner and outer surfaces is installed at a sampling point of ultrapure water production facilities. The hollow fiber membrane 602 has one end sealed with an adhesive 604 (urethane resin) and bonded and fixed to a nipple (PT½) 603 made of polyvinylidene fluoride with the adhesive 604 (urethane resin). The nipple 603 has a screw A part 605 and a screw B part 606. In this example, the screw A part 605 is a normal ½-inch size PT screw, so that it can be easily attached to the sampling point. Incidentally, the screw B part 606 may be used as an external cylinder to collect a filtrate after fine particles are trapped.

Then, a prescribed volume of ultrapure water is passed from the opening side of the hollow fiber membrane 602 and finally water remaining on the inner surface side of the hollow fiber membrane 602 is sucked to the last drop from the filtered water side. After this, the device 601 is detached in the same procedure as when being installed, and the number of blank particles is measured with the scanning electron microscope. A result thereof is 1×10⁴ particles/100 mm². This value is nearly equal to that in Table 5 showing the results of, prior to the sampling, measuring the numbers of blank particles (numbers of contamination fine particles) using a hollow fiber membrane of the same production lot as the hollow fiber membrane 602 used for the sampling and those of plural different lots A to E. This shows that contamination dramatically decreases because of easy attachment to and detachment from a sample introducing line.

Example 7

Figure 9:
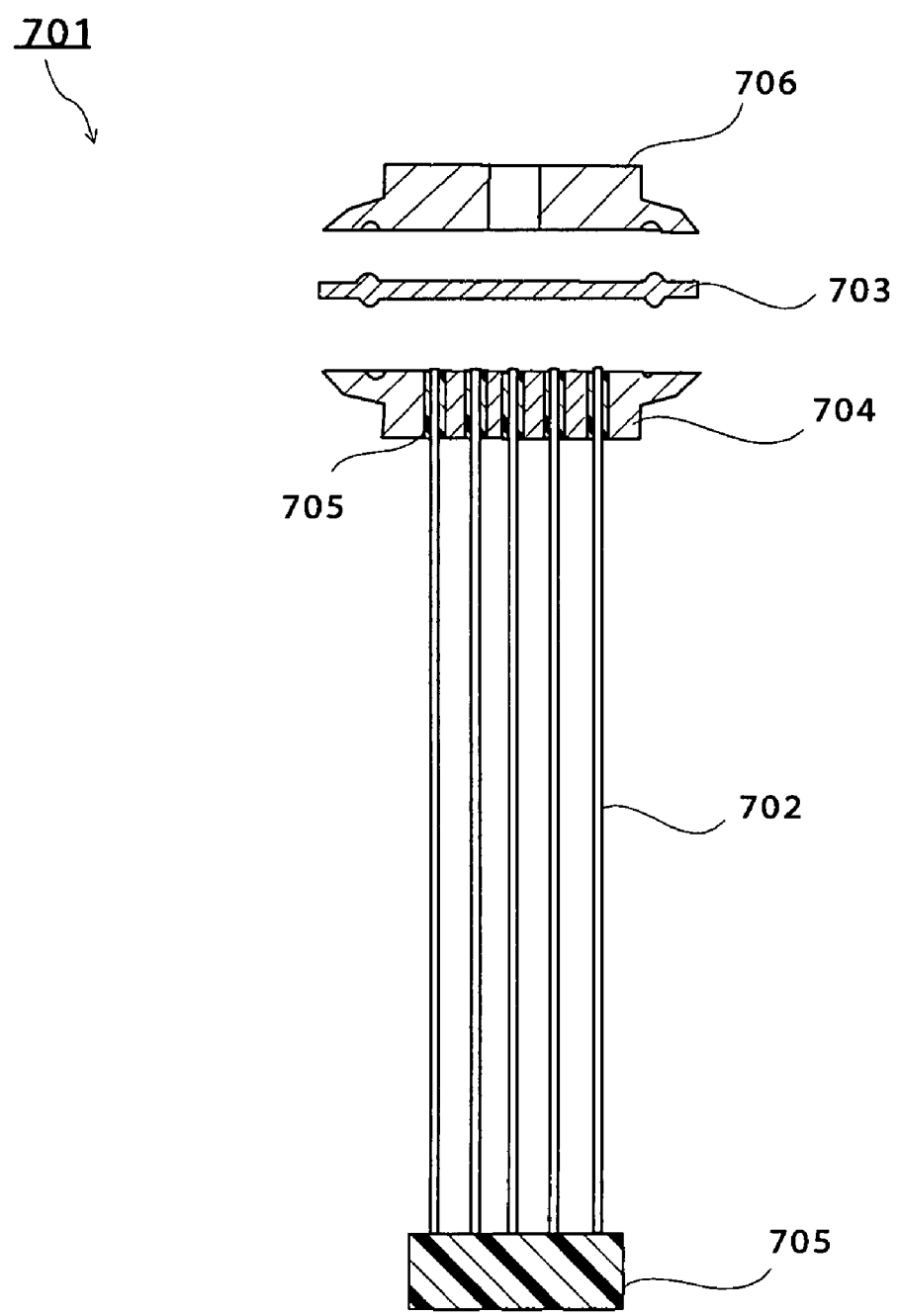
FIG. 9 is a sectional view showing the constitution of a filtration device for measuring the number of fine particles according to Example 7.

The number of fine particles in the ultrapure water is measured using a filtration device for measuring the number of fine particles 701 shown in FIG. 9.

As shown in FIG. 9, the filtration device 701 (hollow fiber membrane module) using an UF hollow fiber membrane 702 (a nominal molecular weight cutoff of 10,000, a hollow fiber membrane outer diameter/inner diameter=1.4 mm/0.6 mm) which is made of polysulfone and manufactured by Asahi Kasei Chemicals Corporation and has a skin layer in each of an inner and outer surfaces is installed at the sampling point of the ultrapure water production system. The hollow fiber membrane 702 has one end sealed with an adhesive 705 (epoxy resin) and bonded and fixed to a 1S stainless-steel ferrule joint 704 with the adhesive 705 (epoxy resin). The hollow fiber membrane 702 bonded and fixed to this ferrule joint 704 is fixed to a 1S stainless-steel ferrule joint 706 (PT¼, with screws) for attachment to the sampling point by 1S ferrule packing 703. In this example, the device 701 can be attached to the sampling point by the 1S ferrule packing 703 through one-touch operation, which offers more simplicity.

Then, after a prescribed volume of ultrapure water is passed from the opening end side of the hollow fiber membrane 702 and finally water remaining on the inner surface side of the hollow fiber membrane 702 is sucked to the last drop from the filtered water side, the device 701 is detached in the same procedure as when being installed, and the number of blank particles is measured with the scanning electron microscope in the same manner as in Example 6. A result thereof is $1\times10^4$ particles/100 mm$^2$. This value is nearly equal to that in Table 5 showing the results of, prior to the sampling, measuring the numbers of blank particles (numbers of contamination fine particles) using a hollow fiber membrane of the same production lot as the hollow fiber membrane 702 used for the sampling and those of plural different lots A to E. This shows that contamination dramatically decreases because the device 701 can be easily attached to and detached from a sample line.

TABLE 1

|  |  | Example 1 | Comparative Example 1 | Comparative Example 2 |
|---|---|---|---|---|
| Filtration Membrane Conditions | Number of Blank Particles [particles/cm$^2$] | 2.E+04 | — | 5.E+06 |
|  | Filtration Flux [ml/cm$^2$/min/0.2 MPa/25° C.] | 1.8 | 0.2 | 2.5 |
|  | Effective Filtraition Area [cm$^2$] | 3.1 | 3.1 | 3.1 |
|  | Pore Diameter (Molecular Weight Cutoff) | 0.02 (10,000) | 0.03 µm | (100,000) |
| Filtration Test Results | Filtration volume [L] | 78 | Unusable | Unusable |
|  | Number of Days of Filtration [days] | 10 |  |  |
|  | Number of Counting Fields | 1000 |  |  |
|  | Counting Field Area [mm$^2$] | 0.033 |  |  |
|  | Value of Countable Fine Particles (containing Blank Particles) [particles] | 45 |  |  |
|  | Number of Blank Particles [particles] | 8 |  |  |
|  | Number of Trapped Particles [particles] | 37 |  |  |
|  | Number of Particles Required to Calculate Particle Number Concentraition [particles]* | 20 |  |  |
|  | Fine Particle Number Concentration [particles/ml] | 5 |  |  |

*Number of Particles Required to Calculate Particle Number Concentration: Largest Number of [20 particles], [Same Number as Number of Blank Particles], [Standard Deviation of Number of Blank Particles × 3] Required Particle Number is 20 in this Example

TABLE 2

|  |  | Example 2 |  | Comparative Example 3 | Comparative Example 4 |
|---|---|---|---|---|---|
| Filtration Membrane Conditions | Number of Blank Particles [particles/cm$^2$] | 1.E+04 |  | 2.E+05 | 2.E+06 |
|  | Filtration Flux [ml/cm$^2$/min/25° C.] | 1.8 |  | 0.2 | 2.5 |
|  | Effective Filtraition Area [cm$^2$] | 3.1 |  | 3.1 | 3.1 |
|  | Pore Diameter (Molecular Weight Cutoff) | 0.03(10,000) |  | 0.03 µm | (100,000) |
| Filtration Test Results | Filtration volume [L] | 78 | 78 | 9 | 113 |
|  | Number of Days of Filtration [days] | 10 | 10 | 10 | 10 |
|  | Number of Counting Fields | 1000 | 300 | 300 | 300 |
|  | Counting Field Area [mm$^2$] | 0.033 | 0.01 | 0.01 | 0.01 |
|  | Value of Countable Fine Particles (containing Blank Particles) [particles] | 26 | 7 | 21 | 211 |
|  | Number of Blank Particles [particles] | 4 | 1 | 20 | 200 |
|  | Number of Trapped Particles [particles] | 22 | 6 | 1 | 11 |
|  | Number of Particles Required to Calculate Particle Number Concentration [particles]* | 20 | 20 | 20 | 200 |
|  | Fine Particle Number Concentration [particles/ml] | 3 | <8 | <70 | <60 |

*Number of Particles Required to Calculate Particle Number Concentration: Largest Number of [20 particles], [Same Number as Number of Blank Particles], [Standard Deviation of Number of Blank Particles × 3] Required Particle Number is 20 in this Example and Comparative Example 3 and Number of Blank Particles in Comparative Example 4

TABLE 3

|  |  | Example 3 | Comparative Example 5 | Comparative Example 6 |
|---|---|---|---|---|
| Filtration Membrane Conditions | Number of Blank Particles [particles/cm$^2$] | 1.E+04 | 2.E+05 | 2.E+06 |
|  | Filtration Flux [ml/cm$^2$/min/0.2 MPa/25° C.] | 1.8 | 0.2 | 2.5 |
|  | Effective Filtraition Area [cm$^2$] | 3.1 | 3.1 | 3.1 |
|  | Pore Diameter (Molecular Weight Cutoff) | 0.03 (10,000) | 0.03 μm | (100,000) |
| Filtration Test Results | Filtration volume [L] | 25 | 25 | 250 |
|  | Number of Days of Filtration [days] | 3 | 28 | 22 |
|  | Number of Counting Fields | 300 | 300 | 300 |
|  | Counting Field Area [mm$^2$] | 0.01 | 0.01 | 0.01 |
|  | Value of Countable Fine Particles (containing Blank Particles) [particles] | 21 | 42 | 415 |
|  | Number of Blank Particles [particles] | 1 | 20 | 200 |
|  | Number of Trapped Particles [particles] | 20 | 22 | 215 |
|  | Number of Particles Required to Calculate Particle Number Concentraition [particles]* | 20 | 20 | 200 |
|  | Fine Particle Number Concentration [particles/ml] | 25 | 28 | 27 |

*Number of Particles Required to Calculate Particle Number Concentration: Largest Number of [20 particles], [Same Number as Number of Blank Particles], [Standard Deviation of Number of Blank Particles × 3] Required Particle Number is 20 in this Example and Comparative Example 5 and Number of Blank Particles in Comparative Example 6

TABLE 4

|  |  | Example 4 | Comparative Example 7 | Comparative Example 8 | Comparative Example 9 |
|---|---|---|---|---|---|
| Filtration Membrane Conditions | Number of Blank Particles [particles/cm$^2$] | 5.E+04 | 1.E+07 | 5.E+04 | 5.E+04 |
|  | Filtration Flux [ml/cm$^2$/min/0.5 MPa/25° C.] | 4.2 | 4.7 | 4.2 | 4.2 |
|  | Effective Filtraition Area [cm$^2$] | 0.94 | 3.1 | 0.94 | 0.94 |
|  | Pore Diameter (Molecular Weight Cutoff) | 0.01(10000) | 0.01(100000) | 0.01(10000) | 0.01(10000) |
| Filtration Test Results | Filtration volume [L] | 173 | 648 | 173 | 173 |
|  | Number of Days of Filtration [days] | 30 | 30 | 30 | 30 |
|  | Blow Flow Rate [ml/min] | 100 | 0 | 0 | 100 |
|  | Number of Counting Fields | 1200 | 1200 | 1200 | 1200 |
|  | Counting Field Area [mm$^2$] | 0.01 | 0.01 | 0.01 | 0.01 |
|  | Value of Countable Fine Particles (containing Blank Particles) [particles] | 25 | 420 | 105 | Uncountable |
|  | Number of Blank Particles [particles] | 5 | 400 | 5 | 5 |
|  | Number of Trapped Particles [particles] | 20 | 20 | 100 | — |
|  | Number of Particles Required to Calculate Particle Number Concentraition [particles]* | 20 | 400 | 20 | 20 |
|  | Fine Particle Number Concentration [particles/ml] | 1 | <20 | 5 | Uncalculatable |

*Number of Particles Required to Calculate Particle Number Concentration: Largest Number of [20 particles], [Same Number as Number of Blank Particles], [Standard Deviation of Number of Blank Particles × 3]

TABLE 5

| Lot | Number of Blank Particles Adhering to Inner Surface of Hollow Fiber Membrane Mean Value (number of fine particles/100 mm$^2$) |
|---|---|
| Same as in Example 5 | 1 × 10$^4$ |
| A | 1.9 × 10$^4$ |
| B | 1.9 × 10$^4$ |
| C | 1 × 10$^4$ |
| D | 2.9 × 10$^4$ |
| E | 2.9 × 10$^4$ |

TABLE 6

Number of Fine Particles Observed on Inner Surface of Hollow Fiber Membrane (Number of Fields = 200, 1 Field Area = 6.40 × 10$^{-5}$ mm$^2$, Observation Magnification of 15000-fold)

| N-number | 1 | 2 | 3 | 4 | 5 | Mean |
|---|---|---|---|---|---|---|
|  | 9 | 7 | 6 | 10 | 11 | 8.6 |

INDUSTRIAL APPLICABILITY

A method for measuring the number of fine particles in ultrapure water, a filtration device for measuring the number of fine particles, a method for manufacturing thereof, and a hollow fiber membrane unit for use in the device of the present invention are capable of minimization of a measurable particle diameter, improvement in analytical precision, reduction in filtration time, and simplification. Accordingly, they are suitable as a method for measuring the number of fine particles in ultrapure water containing fine particles with a finer particle diameter, a filtration device for measuring the number of fine particles, and a hollow fiber membrane unit for use in the device.

What is claimed is:

1. A method for measuring the number of fine particles in ultrapure water using a filtration device for measuring the number of fine particles in ultrapure water, the filtration device comprising:

a hollow fiber membrane unit constituted by sealing one end of a hollow fiber membrane having a skin layer capable of trapping the fine particles in the ultrapure water at least on an inner surface thereof by setting a pore diameter of the skin layer equal to or less than a particle diameter of each of the fine particles and fixing a fixing member to an outer periphery between the sealed portion and an open portion via a resin mold part;

a water drain part external cylinder connected to one side of the fixing member while internally equipped with the sealed portion of the hollow fiber membrane; and a water supply part external cylinder connected to the other side of the fixing member while internally equipped with the open portion of the hollow fiber membrane and having a water supply port and a blow water drain port through which the ultrapure water supplied from the water supply port is discharged, the method, comprising:

passing the ultrapure water from the water supply port of the water supply part external cylinder toward the blow water drain port;

subjecting the ultrapure water to internal pressure filtration through the hollow fiber membrane while discharging part of the ultrapure water supplied from the water supply port of the water supply part external cylinder to the blow water drain port;

exposing the inner surface of the hollow fiber membrane; and measuring the number of fine particles on the exposed inner surface.

2. The method for measuring the number of fine particles in the ultrapure water according to claim 1, wherein the hollow fiber membrane has the skin layer on each of the inner and an outer surface thereof.

3. A method for manufacturing a filtration device for measuring the number of fine particles in ultrapure water, comprising:

forming a hollow fiber membrane unit with both ends sealed by sealing both ends of a hollow fiber membrane having a skin layer capable of trapping the fine particles in the ultrapure water at least on an inner surface thereof and fixing a fixing member to an outer periphery of a central portion thereof with a resin mold;

connecting the fixing member of the hollow fiber membrane unit with both ends sealed to a water drain part external cylinder internally equipped with the hollow fiber membrane and reversely passing push water having an antibacterial effect from a water drain port side of the water drain part external cylinder as well as cutting one end of the hollow fiber membrane; and connecting a water supply part external cylinder to the cut one end side of the hollow fiber membrane and reversely passing the push water having the antibacterial effect to fill an interior of the filtration device therewith.

* * * * *